(12) United States Patent
Izu et al.

(10) Patent No.: US 9,216,305 B2
(45) Date of Patent: Dec. 22, 2015

(54) CORE-SHELL-TYPE CERIUM OXIDE MICROPARTICLE, DISPERSION SOLUTION COMPRISING THE MICROPARTICLE, AND PROCESS FOR PRODUCTION OF THE MICROPARTICLE OR DISPERSION SOLUTION

(75) Inventors: Noriya Izu, Aichi (JP); Ichiro Matsubara, Aichi (JP); Woosuck Shin, Aichi (JP); Toshio Itoh, Aichi (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 270 days.

(21) Appl. No.: 12/444,799

(22) PCT Filed: Oct. 9, 2007

(86) PCT No.: PCT/JP2007/069708
§ 371 (c)(1),
(2), (4) Date: Apr. 8, 2009

(87) PCT Pub. No.: WO2008/044685
PCT Pub. Date: Apr. 17, 2008

(65) Prior Publication Data
US 2010/0015188 A1 Jan. 21, 2010

(30) Foreign Application Priority Data
Oct. 10, 2006 (JP) .................. 2006-276871
Oct. 5, 2007 (JP) .................. 2007-262578

(51) Int. Cl.
*C01F 1/00* (2006.01)
*A61Q 17/04* (2006.01)
(Continued)

(52) U.S. Cl.
CPC .............. *A61Q 17/04* (2013.01); *A61K 8/0275* (2013.01); *A61K 8/11* (2013.01); *A61K 8/19* (2013.01);
(Continued)

(58) Field of Classification Search
USPC ........................................... 502/159
See application file for complete search history.

(56) References Cited

U.S. PATENT DOCUMENTS 5,006,318 A 4/1991 Demazeau et al.
6,752,979 B1 6/2004 Talbot et al.
(Continued)

FOREIGN PATENT DOCUMENTS

JP 63 502656 10/1988
JP 2 92810 4/1990
(Continued)

OTHER PUBLICATIONS

"Morphology—Controllable Synthesis of Mesoporous CeO2 Nano and Microstructures" by Chunman Ho et al. CHem. mater. 2005, 17, 4514-4522.*

(Continued)

*Primary Examiner* — Melvin C Mayes
*Assistant Examiner* — Colette Nguyen
(74) *Attorney, Agent, or Firm* — Suzannah K. Sundby, Esq.; Canady + Lortz LLP

(57) ABSTRACT

An object of the present invention is to provide a core-shell-type cerium oxide microparticle, a dispersion solution comprising the microparticle, and a process for production of the microparticle or dispersion solution, and to achieve the object, the present invention provides a core-shell-type cerium oxide microparticle which has an average particle diameter of 30 to 200 nm and a coefficient of variation therein no greater than 0.25, and in which the secondary particle forming the core portion is spherical in shape and a polymer is attached to its surface, a dispersion solution of this cerium oxide microparticle and a dry powder from the cerium oxide microparticle dispersion solution, and a process of producing a core-shell-type cerium oxide microparticle or a dispersion solution thereof, which comprises the steps of: mixing a cerium salt and a polymer in an organic solvent to obtain a mixture; and heating this mixture under reflux at a prescribed temperature to precipitate core-shell-type cerium oxide microparticles, wherein the cerium salt is cerium nitrate and the particle diameter of the microparticles is adjusted using the molecular weight of the polymer.

14 Claims, 17 Drawing Sheets

(51) Int. Cl.

| | | |
|---|---|---|
| *A61K 8/02* | (2006.01) | |
| *A61K 8/11* | (2006.01) | |
| *A61K 8/19* | (2006.01) | |
| *A61K 8/73* | (2006.01) | |
| *A61K 8/81* | (2006.01) | |
| *B01J 13/14* | (2006.01) | |
| *B82Y 30/00* | (2011.01) | |
| *C01F 17/00* | (2006.01) | |

(52) U.S. Cl.
CPC ............... *A61K 8/731* (2013.01); *A61K 8/8176* (2013.01); *B01J 13/14* (2013.01); *B82Y 30/00* (2013.01); *C01F 17/0043* (2013.01); *A61K 2800/413* (2013.01); *A61K 2800/437* (2013.01); *A61K 2800/624* (2013.01); *C01P 2002/82* (2013.01); *C01P 2002/84* (2013.01); *C01P 2002/88* (2013.01); *C01P 2004/02* (2013.01); *C01P 2004/03* (2013.01); *C01P 2004/04* (2013.01); *C01P 2004/32* (2013.01); *C01P 2004/52* (2013.01); *C01P 2004/64* (2013.01); *C01P 2004/84* (2013.01); *Y10T 428/2998* (2015.01)

(56) References Cited

U.S. PATENT DOCUMENTS

| | | | |
|---|---|---|---|
| 2003/0008938 A1* | 1/2003 | Sano et al. | 523/160 |
| 2003/0032679 A1 | 2/2003 | Cayton et al. | |
| 2005/0065026 A1 | 3/2005 | Okubo | |

FOREIGN PATENT DOCUMENTS

| | | | |
|---|---|---|---|
| JP | 6 218276 | | 8/1994 |
| JP | 06-218276 | * | 8/1994 |
| JP | 2002 201023 | | 7/2002 |
| JP | 2002 255515 | | 9/2002 |
| JP | 2003 347245 | | 12/2003 |
| JP | 2004 35632 | | 2/2004 |
| JP | 2004 513869 | | 5/2004 |
| JP | 2005 97642 | | 4/2005 |
| JP | 2005 519756 | | 7/2005 |
| JP | 2006 8629 | | 1/2006 |
| WO | 2005 040447 | | 5/2005 |

OTHER PUBLICATIONS

Characterization of CeO2 Fine Particles Prepared by the Homogeneous Precipitation Method With a Mixed Solution of Ethylene Glycol and Polyethylene Glycol. Naofumi Uekawa.*

Ho, C. et al., "Morphology—Controllable Synthesis of Mesoporous CeO Nano-And Microstructures", Chemistry of Materials, vol. 17, No. 17, pp. 4514-4522 (2005).

Si, R. et al., "Self-Organized Monolayer of Nanosized Ceria Colloids Stabilized by Poly(Vinylpyrrolidone)", Journal of Physical Chemistry B, vol. 110, No. 12, pp. 5994-6000 (2006).

Lakhwani, S. et al, "Adsorption of Polyvinylpyrrolidone (PVP) and Its Effect on the Consolidation of Suspensions of Nanocystalline $CeO_2$ Particles", Journal of Materials Science, vol. 34, No. 16, pp. 3909-3912 (1999).

Shibata, S., Seramikkusu, vol. 41, No. 5, pp. 334-335 (2006).

Krishna, M. G. et al., "Temperature and Ionic Size Dependence of the Properties of Ceria Based Optionic Thin Films", Materials Science and Engineering, vol. B55, pp. 14-20 (1998).

Mogensen, M. et al., "Physical, Chemical and Electrochemical Properties of Pure and Doped Ceria", Solid State Ionics, vol. 129, pp. 63-94 (2000).

Uekawa, N., "Characterization of $CeO_2$ Fine Particles Prepared by the Homogeneous Precipitation Method With a Mixed Solution of Ethylene Glycol and Polyethylene Glycol", J. Mater. Res., vol. 19, No. 4, pp. 1087-1092 (2004).

Chu, X., "Sintering of Sol-Gel-Prepared Submicrometer Particles Studied by Transmission Electron Microscopy", J. Am. Ceram. Soc., vol. 76, No. 8, pp. 2115-2118 (1993).

Hsu, W. P. et al., "Preparation and Properties of Monodispersed Colloidal Particles of Lanthanide Compounds. 2. Cerium (IV)", Langmuir, vol. 4, No. 1, pp. 31-37 (1988).

Yang, H. et al., "Synthesis of Homogeneous PVP-Capped $SnS_2$ Submicron Particles Via Microwave Irradiation", Materials Letters, vol. 60, pp. 3714-3717 (2006).

Zhang, Z. et al., "PVP Protective Mechanism of Ultrafine Silver Powder Synthesized by Chemical Reduction Processes", Journal of Solid State Chemistry, vol. 121, pp. 105-110 (1996).

Tao, D. et al., "New Procedure Towards Size-Homogeneous and Well-Dispersed Nickel Oxide Nanoparticles of 30 NM", Materials Letters, vol. 58, pp. 3226-3228 (2004).

Xi, G. et al., "Selected-Control Synthesis of $PbO_2$ Submicrometer-Sized Hollow Spheres and $Pb_3O_4$ Microtubes", Inorganic Chemistry Communications, vol. 7, pp. 607-610 (2004).

* cited by examiner

CORE-SHELL-TYPE CERIUM OXIDE MICROPARTICLE, DISPERSION SOLUTION COMPRISING THE MICROPARTICLE, AND PROCESS FOR PRODUCTION OF THE MICROPARTICLE OR DISPERSION SOLUTION

TECHNICAL FIELD

The present invention relates to a core-shell-type cerium oxide microparticle, a dispersion solution comprising the microparticle, and a process for production of the microparticle or dispersion solution. More particularly, the present invention relates to a process of production of a core-shell-type cerium oxide microparticle or a dispersion solution comprising the microparticle in order to produce the cerium oxide microparticle or the dispersion solution comprising the microparticle, and products thereof, that can be used, for example, for catalysts, photonic crystals, gas sensors, chemical-mechanical polishes, and ultraviolet blocking agents.

BACKGROUND ART

Microparticle-based photonic crystals have quite recently attracted attention (Nonpatent Document 1). This is because light emission and light propagation can be artificially controlled by microparticles. The following properties are required of microparticles for photonic crystal applications: spherical shape, particle diameter about 50 to 200 nm, a small particle diameter distribution (standard deviation on the particle diameter), a high refractive index (n>2), and excellent dispersibility in liquids. Microparticles that satisfy these conditions have not been reported to date. However, cerium oxide has a high refractive index at 2.1 (Nonpatent Documents 2 and 3) and is well suited as a material for photonic crystal applications.

Cerium oxide is also a material well known as an ultraviolet blocking agent, and, for example, an ultraviolet blocking agent that uses cerium oxide has been disclosed in a prior document (Patent Document 1). An ultraviolet blocking agent comes into contact with human skin when used in a cosmetic. Chemical inertness is therefore desired for this component. To date, coating with silica has been reported for inhibiting the chemical activity of cerium oxide. Such cerium oxide microparticles having a chemically inert inorganic material or organic material coated on the surface thereof are promising candidates as ultraviolet blocking agents.

While several reports have appeared to date on the synthesis of cerium oxide nanoparticles (Nonpatent Documents 4 to 7, Patent Document 2), these reports do not contain a description of the dispersibility in liquids or a description of the scatter in the particle diameter of the microparticles. That is, there has been no report of a spherical cerium oxide microparticle that has a particle diameter of about 30 to 200 nm, a small particle diameter distribution (standard deviation on the particle diameter), and an excellent dispersibility in liquids, nor has there been a report with respect to a cerium oxide microparticle dispersion solution.

With regard to the production of a cerium oxide microparticle dispersion solution for the applications cited above, a stable dispersion solution cannot be obtained just by simply drying cerium oxide microparticles and dispersing the cerium oxide microparticles in a dispersion medium by ordinary methods. This is due to the necessity, in order to obtain a stable dispersion solution, for breaking up the aggregation of the cerium oxide microparticles once they have become aggregated. Regardless of whether a gas-phase process or liquid-phase process is used to synthesize nanoparticles, nanoparticles typically undergo strong aggregation after their production unless aggregation is inhibited. Once nanoparticles have undergone strong aggregation, it is generally quite difficult to break up the aggregation even by implementing a deaggregation process.

A mechanical deaggregation technology using ceramic beads has been disclosed in a prior document (Patent Document 3), but the admixture of impurities is considered to be a problem here. The addition of a dispersing agent to the solvent is also required. Based on the preceding discussion, there is a requirement for the synthesis of easily dispersible (aggregation-resistant) cerium oxide microparticles, wherein the deaggregation method is not a mechanical procedure and the addition of a dispersing agent is not required.

Given the great difficulty of eliminating nanoparticle aggregation once it has occurred, the acquisition of easily dispersible cerium oxide microparticles can be envisioned if an aggregation-inhibiting treatment could be carried out prior to aggregation, that is, at the same time as nanoparticle production. When a dispersion medium containing polymer dissolved therein is used as the reaction milieu at this time, aggregation can be inhibited at the same time as cerium oxide microparticle production and a stable cerium oxide microparticle dispersion solution is thereby obtained. In addition, even when the cerium oxide microparticle dispersion solution is dried, due to the implementation of the aggregation-inhibiting treatment facile dispersion can be expected when this is redispersed in a redispersion medium.

While there have been no reports with regard to cerium oxide, there are examples of the application of this concept to the sol-gel method and hydrolysis method (Nonpatent Documents 8 to 11, Patent Document 4). However, to date there have been no examples of the application of this concept to a reflux method in which cerium oxide microparticle precipitation is brought about.

While prior documents do disclose, respectively, a metal oxide ultramicroparticle and a method of producing same and also a metal oxide microparticle (Patent Documents 5 and 6), the aforementioned prior documents in no way describe, for example, a core-shell-type cerium oxide microparticle that has a particle diameter of about 30 to 200 nm and a small metal oxide particle diameter distribution (standard deviation on the particle diameter), that is a spherical secondary particle comprising aggregated metal oxide primary particles having particle diameters of approximately 1 to 3 nm, and that exhibits a good dispersibility in liquids, nor do they describe a core-shell-type cerium oxide microparticle dispersion solution.

Patent Document 1: Japanese Patent Application Laid-open No. 2004-35632
Patent Document 2: Japanese Patent Application Laid-open No. 2002-255515
Patent Document 3: Japanese Patent Application Laid-open No. 2004-35632
Patent Document 4: Japanese Patent Application Laid-open No. H2-92810
Patent Document 5: Japanese Patent Application Laid-open No. H6-218276
Patent Document 6: Japanese Patent Application Laid-open No. 2006-8629
Nonpatent Document 1: Shuichi Shibata, *Seramikkusu*, 41 (2006) 334.
Nonpatent Document 2: M. G. Krishna, A. Hartridge, A. K. Bhattacharya, *Materials Science and Engineering*, B55 (1998) 14.

Nonpatent Document 3: M. Mogensen, N. M. Sammes, G. A. Tompsett, *Solid State Ionics* 129 (2000) 63.

Nonpatent Document 4: C. Ho, J. C. Yu, T. Kwong, A. C. Mak, S. Lai, *Chem. Mater.,* 17 (2005) 4514.

Nonpatent Document 5: N. Uekawa, M. Ueta, Y. J. Wu, K. Kakegawa, *J. Mater. Res.,* 19 (2004) 1087.

Nonpatent Document 6: X. Chu, W. Chung, L. D. Schmidt, *J. Am. Ceram. Soc.,* 76 (1993) 2115.

Nonpatent Document 7: W. P. Hsu, L. Ronnquist, E. Matijevic, *Langmuir,* 4 (1988) 31.

Nonpatent Document 8: H. Yang, C. Huang, X. Su, *Materials Letters,* 60 (2006) 3714.

Nonpatent Document 9: Z. T. Zhang, B. Zhao, L. M. Hu, *J. Solid State Chem.,* 121 (1996) 105.

Nonpatent Document 10: D. L. Tao, F. Wei, *Mater. Lett.* 58 (2004) 3226.

Nonpatent Document 11: G. C. Xi, Y. Y. Peng, L. Q. Xu, M. Zhang, W. C. Yu, Y. T. Qian, *Inorg. Chem. Commun.* 7 (2004) 607.

In light of the circumstances outlined above and considering the prior art described hereabove, the present inventors carried out intensive and extensive investigations with the objective of developing a nanosize cerium oxide microparticle that maintains long-term stability due to an inhibition of nanoparticle aggregation, and also with the objective of developing a method of producing a dispersion solution of this nanosize cerium oxide microparticle. The following new knowledge was discovered as a result: the use of a reflux procedure accrues a number of advantages, e.g., an organic solvent can be used and a reaction initiator may not be necessary; in addition, by using a reflux procedure, an inexpensive nitrate salt can be suitably employed as the starting material rather than an expensive alkoxide, a core-shell-type cerium oxide microparticle that resists nanoparticle aggregation can be produced as a result, and a dispersion solution of the core-shell-type cerium oxide microparticle can also be produced as a result. Additional investigations were performed and the present invention was achieved as a result of these additional investigations and the aforementioned discoveries.

DISCLOSURE OF THE INVENTION

Based on the preceding, an object of the present invention is (1) to provide a core-shell-type cerium oxide microparticle that has a particle diameter of approximately 50 to 200 nm, that has a small particle diameter distribution (standard deviation on the particle diameter), that is spherical, and that exhibits an excellent dispersibility in liquids, wherein the secondary particle that is the core portion thereof is also spherical and exhibits a uniform size, and to provide a dispersion solution of this cerium oxide microparticle. An additional object is (2) to provide, by applying the aforementioned concept to the reflux method, a method of producing the aforementioned core-shell-type cerium oxide microparticle and a method of producing a dispersion solution of this cerium oxide microparticle.

The present invention comprises the following technical means in order to achieve the objects cited above.

(1) A core-shell-type cerium oxide microparticle which comprises a core portion and a polymer layer, 1) the core portion thereof is a secondary particle comprising a spherical aggregation of primary particles of cerium oxide; 2) a shape of this secondary particle is uniform; 3) the polymer layer that forms the shell portion is present on the surface of the secondary particle; 4) an average particle diameter of the microparticle is from 30 nm to 200 nm; and 5) a coefficient of variation in particle diameter of the microparticle is less than 0.25.

(2) The core-shell-type cerium oxide microparticle according to (1), wherein 1) the polymer layer comprises polyvinylpyrrolidone (PVP), hydroxypropyl cellulose (HPC), or a polymer related thereto; 2) washing of this layer does not separate the layer from the secondary particle forming the core portion; and 3) this layer is present in a proportion of 15 weight % to 25 weight %.

(3) The core-shell-type cerium oxide microparticle according to (1), wherein the primary particle diameter is from 1 to 3 nm.

(4) A core-shell-type cerium oxide microparticle powder that is a dry powder containing the core-shell-type cerium oxide microparticle defined in any of (1) to (3), which comprises a core-shell-type cerium oxide microparticle powder that 1) has an ability to undergo an excellent dispersion in a dispersion medium that does not contain a dispersing agent; 2) does not undergo sedimentation even after standing for at least one day in the dispersion medium; and 3) also exhibits an excellent dispersibility even after being subjected to a heat treatment.

(5) A cerium oxide microparticle powder, which is obtained by subjecting the core-shell-type cerium oxide microparticle powder defined in (4) to a heat treatment at from 300° C. to 500° C., and which 1) has a ability to undergo an excellent dispersion in a dispersion medium that does not contain a dispersing agent and 2) does not undergo sedimentation even after standing for at least one day in the dispersion medium.

(6) A core-shell-type cerium oxide microparticle dispersion solution comprising the core-shell-type cerium oxide microparticle or core-shell-type cerium oxide microparticle powder defined in any of (1) to (4) dispersed in a dispersion medium.

(7) A cerium oxide microparticle dispersion solution comprising the cerium oxide microparticle powder defined in (5) redispersed in a dispersion medium.

(8) The core-shell-type cerium oxide microparticle dispersion solution or cerium oxide microparticle dispersion solution according to (6) or (7), wherein the dispersion medium is any one of water, ethanol, terpineol, and ethylene glycol or is a mixed solution comprising a mixture of a plurality of selections from water, ethanol, terpineol, and ethylene glycol.

(9) A cosmetic having an ultraviolet blocking action, that contains the microparticle, microparticle powder, or microparticle dispersion solution defined in any of (1) to (8).

(10) A fiber or resin having an ultraviolet blocking action, in which the microparticle, microparticle powder, or microparticle dispersion solution defined in any of (1) to (8) is dispersed.

(11) A gas sensor having a porous cerium oxide thick film obtained using the microparticle, microparticle powder, or microparticle dispersion solution defined in any of (1) to (8) as starting material.

(12) A cerium oxide microparticle aggregate, cerium oxide microparticle photonic crystal, or cerium oxide colloid crystal, in which the core-shell-type cerium oxide microparticles defined in any of (1) to (3) are three dimensionally aggregated.

(13) A process of producing the core-shell-type cerium oxide microparticle, the cerium oxide microparticle powder, or the cerium oxide microparticle dispersion solution defined in any of (1) to (8), comprising the steps of:

mixing a cerium salt and a polymer in a high-boiling organic solvent to obtain a mixture; and heating this mixture under reflux at a temperature of at least 110° C. to precipitate cerium oxide microparticles.

(14) The process of producing the cerium oxide microparticle according to (13), wherein the cerium salt is cerium nitrate.

(15) The production process according to (13) or (14), wherein the concentration of the polymer (weight of polymer added per unit volume of the organic solvent) is from 80 kg/m$^3$ to 120 kg/m$^3$.

(16) The production process according to any of (13) to (15), wherein the average molecular weight of the polymer as polyethylene glycol is 4,000 to 20,000.

(17) The production process according to any of (13) to (16), wherein the particle diameter of the cerium oxide microparticle is made smaller by increasing the average molecular weight of the polymer.

(18) The production process according to any of (13) to (17), wherein the polymer is PVP or HPC.

(19) The production process according to any of (13) to (18), wherein the organic solvent is ethylene glycol.

The present invention is described in additional detail in the following.

The core-shell-type cerium oxide microparticle encompassed by the present invention denotes a microparticle comprising a polymer layer present on the surface of a secondary particle that itself comprises the spherical aggregation of primary particles of cerium oxide (see FIG. 8), and differs from a microparticle comprising a polymer present on the surface of a primary particle or on the surface of a secondary particle that comprises an irregular aggregate of primary particles. A composite particle comprising a polymer compound coated on the surface of a primary particle or an aggregate is disclosed in Patent Document 6; however, this primary particle or aggregate is not spherical and has a nonuniform shape. This is due to the use in the production method disclosed in this document of a dispersing device, such as a bead mill, to disperse and grind already synthesized metal oxide microparticles.

Grinding occurs in this dispersion step into primary particles or into particles that are primary particle aggregates, and after grinding the primary particle aggregates cannot be spherical and cannot have a uniform size. In addition, this document also teaches a proportion of at least 25 weight % for the polymer coating, while in the present invention this is 15 to 25 weight %, vide infra, and the polymer layer is thus less than 25 weight %. This is because the easily freed polymer is removed by washing. This also represents a major difference from the composite particle of the aforementioned document. When the diameter of the core portion is 85 nm, the layer comprising the shell region has a thickness of about 10 nm.

The present invention encompasses a core-shell-type cerium oxide microparticle wherein the average particle diameter of the core-shell-type cerium microparticle is from 30 nm to 200 nm, the coefficient of variation for the core-shell-type cerium oxide microparticle is no more than 0.25, the secondary particle forming the core portion has a spherical shape, the shape of this secondary particle is spherical and the size is uniform, and a polymer comprising the shell portion is attached on the surface of the cerium oxide secondary particle. The present invention additionally encompasses a core-shell-type cerium oxide microparticle dispersion solution provided by the dispersion of the preceding core-shell-type cerium oxide microparticle in a dispersion medium.

The present invention further encompasses a powder of the aforementioned core-shell-type cerium oxide microparticle, wherein the powder exhibits a good dispersibility in a dispersion medium without the addition of a dispersing agent, does not sediment when allowed to stand for at least one day, and exhibits an excellent dispersibility even after heat treatment. The present invention additionally encompasses a process of producing a core-shell-type cerium oxide microparticle, a cerium oxide microparticle, or a cerium oxide microparticle dispersion solution, comprising the steps of mixing a cerium salt and a polymer in a high-boiling organic solvent to obtain a mixture and heating this mixture under reflux at a temperature of at least 110° C. to precipitate cerium oxide microparticles, wherein the cerium salt is cerium nitrate and the particle diameter of the cerium oxide microparticles can be adjusted through the molecular weight of the polymer.

The core-shell-type cerium oxide microparticle dispersion solution under consideration refers to a dispersion of the core-shell-type cerium oxide microparticle (the dispersed material) in a dispersion medium, and may also be called a suspension or a sol rather than a dispersion solution. It may also be referred to as a paste when the viscosity is high. The process of producing the core-shell-type cerium oxide microparticle dispersion solution of the present invention will be described first. The starting materials are cerium nitrate, a high-boiling organic solvent, and a polymer. The cerium nitrate may be acquired commercially and is ordinarily a hydrate.

A metal nitrate salt other than cerium nitrate may be added in order to obtain a cerium oxide microparticle to which metal ion has been added. The high-boiling organic solvent is, for example, ethylene glycol (EG), diethylene glycol, glycerol, and so forth, wherein ethylene glycol is more preferred. In addition, the polymer is preferably soluble in the organic solvent and can be exemplified by polyvinylpyrrolidone (PVP), hydroxypropyl cellulose (HPC), polyethylene glycol (PEG), and so forth, wherein polyvinylpyrrolidone (PVP) is more preferred.

These starting materials are mixed and dissolved. This is the step of mixing a cerium salt and a polymer in a high-boiling organic solvent to obtain a mixture. The cerium nitrate concentration at this point is preferably at least 0.4 kmol/m$^3$. Such a concentration is used in order to increase the proportion of the oxide present in the resulting dispersion solution and thereby bring about an increase in the yield. The polymer concentration is preferably from 80 kg/m$^3$ to 120 kg/m$^3$. This polymer concentration is defined as the weight of the added polymer per unit volume of the solvent. The reasons for this 80 kg/m$^3$ to 120 kg/m$^3$ range are as follows: at much below this range, the cerium oxide microparticles readily aggregate and the core-shell configuration is lost; at much above this range, the cerium oxide nucleation reaction does not proceed.

The aforementioned mixture is heated under reflux at from 110 to 190° C. This is the step of heating under reflux at a prescribed temperature to precipitate cerium oxide. A base, such as sodium hydroxide or ammonia, is typically added when the precipitation of an oxide is sought; however, a characteristic feature of the present invention is that the addition of base is not required. The addition of, for example, sodium hydroxide, runs the risk of the admixture of, for example, sodium in the ultimately obtained nanoparticles. The admixture of such impurities is impossible in the present invention since the addition of base or the like is not required.

The heating/refluxing period is from about 10 minutes to 120 minutes. Large amounts of unreacted cerium ion may remain at shorter heating/refluxing times, while organic compounds of cerium may be produced at times that are much longer. Due to these considerations, heating/refluxing times of about 10 to 120 minutes are preferred and times of 30 to 120 minutes are more preferred. The turbidity of the mixture increases during this heating under reflux. Cooling is carried out after heating under reflux for the prescribed period of time. Proceeding in the described manner produces a core-shell-type cerium oxide microparticle dispersion solution comprising core-shell-type cerium oxide microparticles dispersed in an organic solvent in which polymer has been dissolved.

The following is believed to be the mechanism by which the core-shell-type metal oxide microparticles are produced.
1. Primary particles of cerium oxide nucleate in the high-boiling organic solvent (polyol) in which polymer is homogeneously dissolved.
2. The primary particles spherically aggregate. Primary particle nucleation also continues without interruption at this point.
3. Nucleated primary particles collect in a spherical manner on the surface of the aggregated particles (secondary particles).
4. At this point, the cerium oxide acts as a catalyst at the surface of the secondary particle and the polymer and/or organic solvent undergo a crosslinking reaction to form a solid polymer layer.
5. Once the solid polymer layer has undergone sufficient growth, aggregation can no longer occur, forming the core-shell-type cerium oxide microparticle.

The core-shell-type cerium oxide microparticle of the present invention is defined as a core-shell-type cerium oxide microparticle that exhibits the following characteristic features: 1) the core portion is a secondary particle comprising a spherical aggregation of primary particles of cerium oxide, 2) the shape of this secondary particle is uniform, 3) a polymer layer, which forms the shell portion, is present on the surface of this secondary particle, 4) the average particle diameter of the microparticle is 30 nm to 200 nm, and 5) the coefficient of variation in particle diameter of the microparticle is less than 0.25. The polymer layer of the shell portion comprises polyvinylpyrrolidone (PVP), hydroxypropyl cellulose (HPC), or a polymer related thereto. This related polymer is, for example, polymer yielded by crosslinking between PVP, polymer yielded by crosslinking between HPC, polymer yielded by crosslinking between polyol and PVP or HPC, and polymer yielded by crosslinking between polyol. Various of these polymers may be present.

Heat is thought to be necessary for the cerium oxide to exhibit catalytic activity, and it is for this reason that heating under reflux at a temperature of at least 110° C. is necessary. In the case of a lower heating/refluxing temperature, the core-shell configuration is not achieved even if primary particles are produced. The core-shell-type cerium oxide microparticle according to the present invention does not appear unless the primary particles undergo aggregation. In this case, due to the presence of large amounts of unreacted polymer, the evaporation of the solvent yields a cerium oxide/polymer composite composition in which the primary particles have been left behind in a polymer matrix; this is clearly different from the core-shell-type cerium oxide microparticle.

In addition, even when aggregation is produced, a catalytic reaction does not occur at the cerium oxide surface and as a consequence the polymer layer cannot be formed and the result is an aggregated particle with a nonuniform morphology. A metal oxide/polymer composite composition of this nature is disclosed in Patent Document 5. This is essentially different from the present invention. As is shown in the examples provided below, core-shell-type cerium oxide microparticles are not formed below a certain critical temperature, and as a consequence heating under reflux at a high temperature is essential.

The particle diameter of the resulting core-shell-type cerium oxide microparticle can be controlled or adjusted at this point by changing the molecular weight of the polymer. The cerium oxide particle diameter declines as the molecular weight increases within the range of 4,000 to 20,000 for the average molecular weight as polyethylene glycol of the polymer as determined by gel permeation chromatography. The correlation between the molecular weight of the polymer and the cerium oxide particle diameter can be determined in advance, and this can be used to prepare a dispersion solution containing cerium oxide microparticles with a desired particle diameter.

The dispersion medium is the organic solvent used for heating under reflux in the case of the core-shell-type cerium oxide microparticle dispersion solution that is obtained immediately after the aforementioned heating under reflux. Thus, the dispersion medium is ethylene glycol (EG) when the heating under reflux has been run in ethylene glycol (EG). The dispersion medium may be exchanged when it is desired to change the dispersion medium to some other dispersion medium. For example, the dispersion medium can be exchanged by removing the dispersion medium by separating the dispersion medium from the dispersed material by, for example, centrifugal separation, and then adding the desired dispersion medium. During this process, the polymer comprising the shell portion cannot be removed by washing and is indivisible from the core.

It is thought that the polymer used during the heating under reflux remains in the dispersion medium, as does unreacted Ce ion. In view of this, the excess polymer and so forth can be removed by repeating centrifugal separation and solvent exchange. The core-shell-type cerium oxide microparticles, that is, the dispersed material in the dispersion solution obtained by the method described hereabove, are spherical and their particle diameters are approximately equal. This particle diameter is the particle diameter of the core-shell-type cerium oxide microparticle and is the particle diameter determined by observation with a scanning electron microscope (SEM). The secondary particle forming the core portion is an aggregate of primary particles and in some cases is also called a primary aggregate. The primary particle diameter is no greater than 3 nm. The particle that maps on a one-to-one basis to the spherical cerium oxide microparticle comprising the core portion is the secondary particle, not the primary particle. In addition, a monovalent to pentavalent metal ion may also be added to the cerium oxide microparticle. Examples are Na, Ca, Y, Gd, Zr, Hf, Nb, and so forth.

The shape and particle diameter of the cerium oxide microparticles can be evaluated by the following methods. The particle diameter in the dispersion solution immediately after heating under reflux can be determined by dynamic light scattering (DLS). This particle diameter is the particle diameter of particles that occur independently in the dispersion medium. This particle diameter is typically different from the particle diameter of the microparticle as observed by, for example, SEM. The reason for this is that the microparticles frequently undergo additional aggregation in the dispersion medium, in which case it is the size of particles comprising aggregated microparticles that is detected as a result.

The particles yielded by the aggregation of secondary particles (microparticles) are also known as secondary aggregates. The dynamic light scattering (DLS) procedure requires the refractive index of the dispersion medium and the viscosity of the dispersion medium. Literature values can be used for the refractive index of the dispersion medium. The viscosity of the dispersion medium can be taken to be the same as the viscosity of the dispersion solution, and the viscosity of the dispersion solution can be measured and this value can be used. Proceeding in this manner, the average particle diameter $d_{average}$ and standard deviation s are determined and the coefficient of variation $c=s/d_{average}$ is then calculated. In addition, centrifugal separation of the dispersion solution obtained by the hereabove-described method and redispersion in water or ethanol is carried out approximately three times and a dry powder is obtained by drying at, for example, 80° C. This is observed by SEM and the shape, average particle diameter, and standard deviation are then determined.

The average particle diameter of the core-shell-type cerium oxide microparticle is from 30 nm to 200 nm and its coefficient of variation is no greater than 0.25 and preferably is no greater than 0.16. This can be determined by SEM observation of the dry powder. In addition, the particle diameter in the dispersion medium is no more than twice that of the core-shell-type cerium oxide microparticle and preferably is no more than 1.5-times and more preferably is no more than 1.3-times that of the core-shell-type cerium oxide microparticle. This shows that the core-shell-type cerium oxide microparticles are present in the dispersion medium with almost no aggregation.

A polymer layer is of course also present in the shell portion at the surface of the core-shell-type cerium oxide microparticle. This can be examined and identified by Fourier-transform infrared spectrophotometric (FTIR) analysis and thermogravimetric (TG) analysis on the aforementioned dry powder. Since this dry powder is obtained by carrying out centrifugal separation and redispersion in water or ethanol approximately three times, excess polymer unassociated with the core-shell-type cerium oxide microparticle is removed. The dispersion medium is also thoroughly removed due to the drying process. The proportion for the polymer layer is preferably from 15 to 25 weight % and more preferably is from 19 to 22 weight %.

Thus, non-cerium oxide absorption peaks observed by Fourier-transform infrared spectrophotometry (FTIR) are caused by species present at the surface of the cerium oxide microparticles. The fact that this resembles the absorption of a polymer and that weight changes occur at temperatures higher than the boiling point of the dispersion medium leads to the conclusion that a polymer is attached on the surface of the cerium oxide microparticle. This polymer is preferably, for example, PVP, HPC, polymer yielded by crosslinking between PVP, polymer yielded by crosslinking between HPC, polymer yielded by crosslinking between polyol and PVP or HPC, polymer yielded by crosslinking between polyol, and products of the reaction of the preceding with cerium oxide. The polymer at the microparticle surface can also be observed by transmission electron microscopy (TEM).

It is thought that the cerium oxide microparticle obtained according to the present invention is chemically inert due to the attachment of the polymer to the cerium oxide surface. With regard to application as an ultraviolet blocking agent, the microparticles are desirably chemically inert due to the direct contact with, for example, human skin. It is thus thought that the cerium oxide microparticles obtained according to the present invention will be excellent as an ultraviolet blocking agent. In particular, PVP is known to be completely nontoxic for humans and a dispersion solution of cerium oxide microparticles having a PVP coated at the surface therefore has promise as an ultraviolet blocking agent.

An ultraviolet blocking effect can also be expected for articles obtained by dispersing the ultraviolet-blocking cerium oxide microparticles in, for example, a resin, and molding this into a freely selected shape, e.g., a fiber or bulk article. Because the cerium oxide microparticle dispersion solution is extremely stable, a porous cerium oxide thick film can be easily and conveniently formed therefrom and the resulting thick film will be composed of spherical microparticles having uniform particle diameters. Due to this microstructure the thick film will function effectively as a gas sensor.

The dry powder is also easy to disperse when redispersion in a dispersion medium is carried out. This is a property different from that of ordinary powders. As a general matter, a powder undergoes tight aggregation when dried once and as a consequence is not easily dispersed when its redispersion is sought. However, the dry powder of the present invention can be easily redispersed, for example, using just an ultrasound homogenizer, and without requiring a dispersing agent.

The dispersion medium here may be freely selected and is suitably, for example, any one of water, ethanol, terpineol, and ethylene glycol or is a mixed solution comprising a mixture of a plurality of selections from water, ethanol, terpineol, and ethylene glycol. Even when the aforementioned core-shell-type cerium oxide microparticle is redispersed in these media, the particle diameter in the dispersion medium is no more than twice the particle diameter determined by SEM observation and preferably is no more than 1.5-times and more preferably is no more than 1.3-times the particle diameter determined by SEM observation and the core-shell-type cerium oxide microparticles are present without aggregation. This facile redispersibility is believed to be caused by the presence of the polymer in the shell region of the core-shell-type cerium oxide microparticle. Moreover, the excellent dispersibility is maintained even when the dry powder is additionally subjected to a heat treatment at 300° C. to 500° C. This is thought to be due to the presence of a small amount of polymer or organic compound at the surface of the cerium oxide microparticle even after the application of the heat treatment.

Moreover, the shell region-related polymer is completely removed when baking is carried out at temperatures higher than 500° C. Spherical cerium oxide microparticles are obtained when this is done. These cerium oxide microparticles are secondary particles comprising spherically aggregated primary particles, and when these secondary particles make up the gas detection element of a gas sensor, facile gas diffusion is obtained and an increase in the sensitivity of the gas sensor may therefore be expected. In the case of a microparticle that simply contains primary cerium oxide particles in a polymer matrix, baking leaves just the primary cerium oxide particles and a spherical shape cannot be obtained even if these primary particles have been aggregated. A gas sensor with the aforementioned structure cannot be fabricated using this. Accordingly, the essential structure of the core-shell-type cerium oxide microparticle is completely different from that of the cerium oxide/polymer composite composition. An aggregate itself comprising a three-dimensional aggregation of the cerium oxide microparticles is organized by self-assembly. In addition, when the microparticles of this aggregate are arranged in a periodic manner, the aggregate itself is a photonic crystal and thereby comes to have a variety of optical functionalities.

Whether or not the aggregate is a photonic crystal can be elucidated using the ultraviolet-visible-near infrared spectrum. A photonic band gap occurs in a photonic crystal and reflection originating therewith is therefore present. If reflection caused by a periodic structure can be confirmed in the ultraviolet-visible-near infrared spectrum, then there is a very high likelihood that the aggregate is a photonic crystal. If a reflection considered as originating from a periodic structure is observed in the ultraviolet-visible-near infrared spectrum of an aggregate obtained in accordance with the present invention, the aggregate may be regarded as a photonic crystal. An aggregate in which microparticles are arranged in a periodic manner is also known as a colloid crystal.

Results such as this indicate, on the other hand, that the secondary particle that is the core portion is spherical and the particle diameters thereof are uniform. This is because such a phenomenon is not seen when the core-shell as a whole is spherical and monodisperse but the core portion is not.

The present invention accrues the following effects.

(1) The present invention provides a core-shell-type cerium oxide microparticle that has a particle diameter of about 50 nm to 200 nm, that has a small particle diameter distribution (standard deviation of the particle diameter), that is spherical, and that exhibits an excellent dispersibility in liquids. The present invention also provides a dispersion solution of this core-shell-type cerium oxide microparticle.

(2) The present invention provides an easily redispersible dry powder of core-shell-type cerium oxide microparticles.

(3) The core-shell-type cerium oxide microparticle dispersion solution of the present invention retains its excellent dispersibility even when subjected to an additional heat treatment.

(4) The present invention provides a dispersion solution comprising core-shell-type cerium oxide microparticles dispersed in a freely selected dispersion medium.

(5) The present invention can provide a high-viscosity core-shell-type cerium oxide microparticle dispersion solution, i.e., a core-shell-type cerium oxide microparticle paste.

(6) The present invention provides a convenient method of producing a core-shell-type cerium oxide microparticle and a convenient method of producing a dispersion solution of this cerium oxide microparticle.

(7) The present invention enables the average particle diameter of the produced microparticle to be freely adjusted by changing the molecular weight of the polymer that is added during the production of the microparticle dispersion solution.

(8) A high-concentration cerium oxide microparticle dispersion solution is obtained.

(9) A spherical cerium oxide microparticle can be obtained by oxidative elimination of the polymer by baking.

(10) The spherical cerium oxide microparticle can be a starting material for photonic crystals.

BEST MODE FOR CARRYING OUT THE INVENTION

Figure 1:
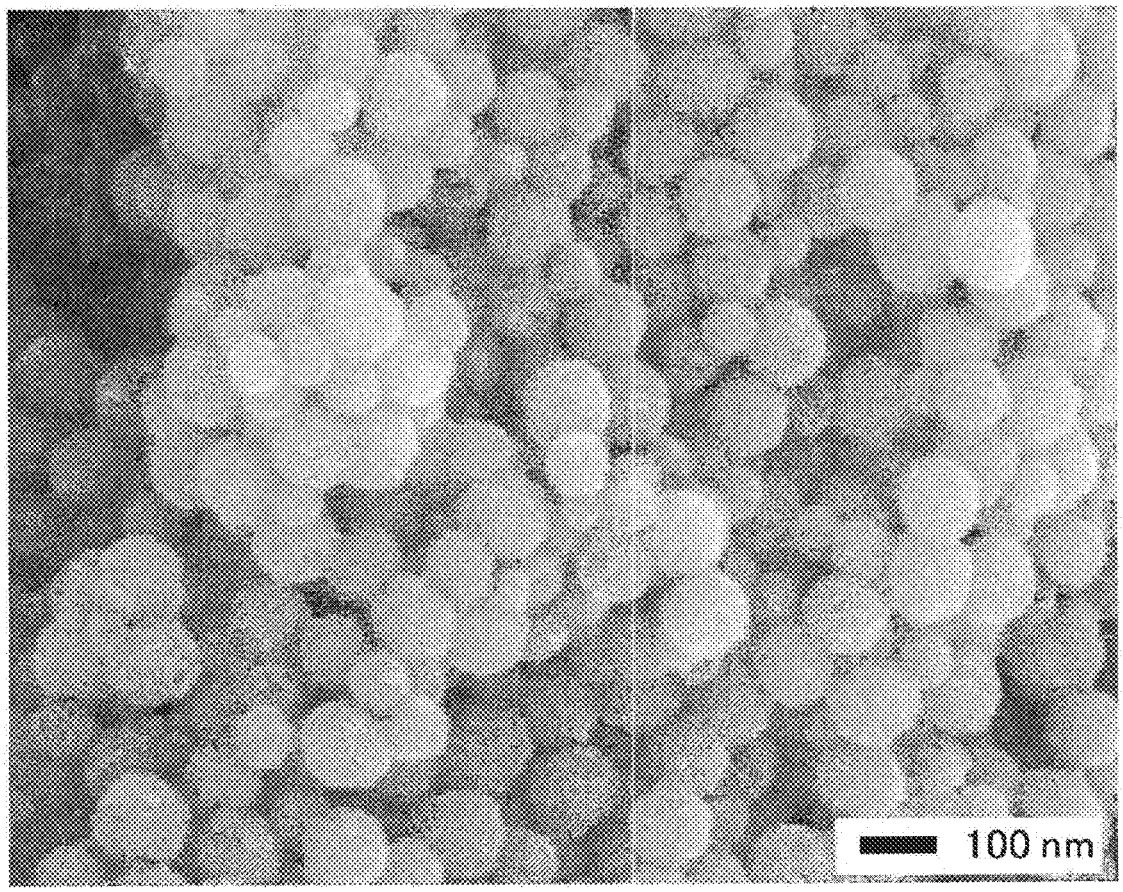
FIG. 1 shows an SEM image of sample 2-2.

The present invention is specifically described based on the examples provided below, but the present invention is in no way limited by these examples.

Example 1

Polyvinylpyrrolidone (PVP) and a cerium salt were added to 30 cm$^3$ ethylene glycol (EG) (Wako Pure Chemical Industries, Ltd.) and stirred. The concentration of the added PVP was made 16 kg/m$^3$ or 120 kg/m$^3$. The PVP (Sigma-Aldrich) used had an average molecular weight of 10,000 for the catalogue value and 4,350 (as polyethylene glycol) for the analytical value yielded by gel permeation chromatography (GPC). The cerium salt was $(NH_4)_2Ce(NO_3)_6$ (Wako Pure Chemical Industries, Ltd.) or $Ce(NO_3)_3 \cdot 6H_2O$ (Kojundo Chemical Laboratory Co., Ltd.) and was used at a concentration of 0.080, 0.400, or 0.600 kmol/m$^3$.

The mixture was heated and then heated under reflux for the specified period of time at 190° C. The experimental conditions are shown in Table 1. A light brown gas was produced during heating under reflux, after which the solution assumed a white turbidity. Heating under reflux for the specified period of time yielded a mixed solution that exhibited white turbidity. A portion of this turbid white solution was then subjected to centrifugal separation at from 3,000 rpm to 10,000 rpm in order to remove unreacted materials and the excess PVP and washing with water and ethanol was carried out. After this washing, drying at 80° C. yielded a powder. The product in the obtained powder was identified by X-ray diffraction (XRD).

The products identified by XRD are shown in Table 1. Cerium oxide was the product in samples 1-1, 1-2, and 1-3. $Ce(HCOO)_3$ was also present in sample 1-4 in addition to cerium oxide. Samples 1-6 and 1-7 were not cerium oxide. With respect to the essential conditions for obtaining cerium oxide, the use of $Ce(NO_3)_3 \cdot 6H_2O$ as the cerium salt was shown to be preferred. Samples 1-1, 1-2, 1-3, and 1-5 contained only cerium oxide.

A higher starting material concentration is preferred. This is because the production of larger amounts of oxide particles in a single experiment is preferable. Considering then a cerium nitrate concentration of at least 0.400 kmol/m$^3$ on a tentative basis, conditions sufficient for obtaining cerium oxide were shown to be a PVP concentration of 120 kg/m$^3$ or a short heating/refluxing time of 10 to 20 minutes. The heating/refluxing time is preferably as long as possible due to the presence of unreacted cerium ion at short heating/refluxing times. However, when the heating/refluxing time is overly long, the cerium oxide reacts with, for example, the ethylene glycol to produce, for example, $Ce(HCOO)_3$, and as a consequence an optimal heating/refluxing time exists. For the experimental conditions in Example 1, the conclusion was drawn that a heating/refluxing time of from 10 minutes to 120 minutes is preferred.

TABLE 1

| sample no. | type of cerium salt | cerium salt concentration (kmol/m³) | PVP concentration (kg/m³) | time period of heating under reflux (min) | product |
|---|---|---|---|---|---|
| 1-1 | $Ce(NO_3)_3 \cdot 6H_2O$ | 0.600 | 120 | 13 | $CeO_2$ |
| 1-2 Comp. Ex. | $Ce(NO_3)_3 \cdot 6H_2O$ | 0.400 | 16 | 12 | $CeO_2$ |
| 1-3 Comp. Ex. | $Ce(NO_3)_3 \cdot 6H_2O$ | 0.080 | 16 | 120 | $CeO_2$ |
| 1-4 Comp. Ex. | $Ce(NO_3)_3 \cdot 6H_2O$ | 0.400 | 16 | 120 | $Ce(HCOO)_3$ + $CeO_2$ |
| 1-5 | $Ce(NO_3)_3 \cdot 6H_2O$ | 0.600 | 120 | 120 | $CeO_2$ |
| 1-6 Comp. Ex. | $(NH_4)_2Ce(NO_3)_6$ | 0.600 | 120 | 20 | $Ce(HCOO)_3$ |
| 1-7 Comp. Ex. | $(NH_4)_2Ce(NO_3)_6$ | 0.080 | 16 | 120 | $Ce(C_2O_4)(HCOO)$ |

Example 2

PVP (Sigma-Aldrich, average molecular weight of 10,000 for the catalogue value and 4,350 (as polyethylene glycol) for the analytical value yielded by GPC) and $Ce(NO_3)_3 \cdot 6H_2O$ (Kojundo Chemical Laboratory Co., Ltd.) were added to 30 cm³ EG (Wako Pure Chemical Industries, Ltd.) and stirred. The concentration of the added PVP was set at from 16 kg/m³ to 160 kg/m³ (refer to Table 2). The $Ce(NO_3)_3 \cdot 6H_2O$ concentration was set at 0.400 kmol/m³. The mixture was heated and then heating under reflux was carried out for 10 to 20 minutes at 190° C. However, in the case of sample 2-4, the reaction indicated below did not occur even when the heating/refluxing time was extended to 120 minutes.

Sample 2-1 was the same as sample 1-2 of Example 1. In the case of samples 2-1, 2-2, and 2-3, a light brown gas was produced during heating under reflux, after which the solution assumed a white turbidity. Heating under reflux for the prescribed period of time yielded a turbid white mixed solution (the dispersion solution). A portion of this turbid white solution was then subjected to centrifugal separation at from 3,000 rpm to 10,000 rpm in order to remove unreacted materials and the excess PVP and washing with water and ethanol was carried out. Drying the product at 80° C. yielded a powder.

The particle diameter distribution of the dispersion solution was investigated by the DLS method. The viscosity and refractive index of the solvent are required for a determination of the particle diameter by the DLS method. The viscosity of the dispersion solution was determined using a B-type viscometer and this was used as the viscosity of the solvent. The B-type viscometer had a cone and plate geometry. The value for ethylene glycol (1.429) was used for the refractive index. The average particle diameter was determined by cumulant analysis. The powder dried at 80° C. was characterized by XRD and SEM. The long-term stability of the dispersion solution was investigated by introducing the sample into a container and allowing the sample to stand. The experimental conditions and experimental results are shown in Table 2.

Figure 2:
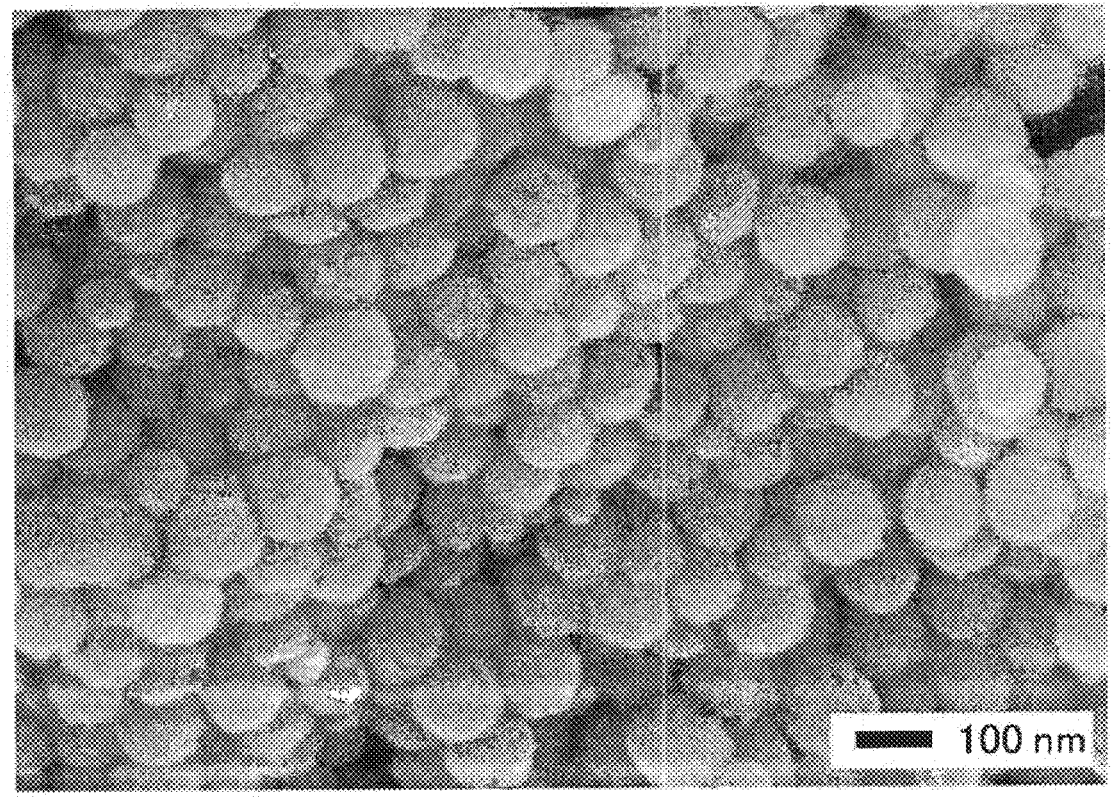
FIG. 2 shows an SEM image of sample 2-3.
Figure 3:
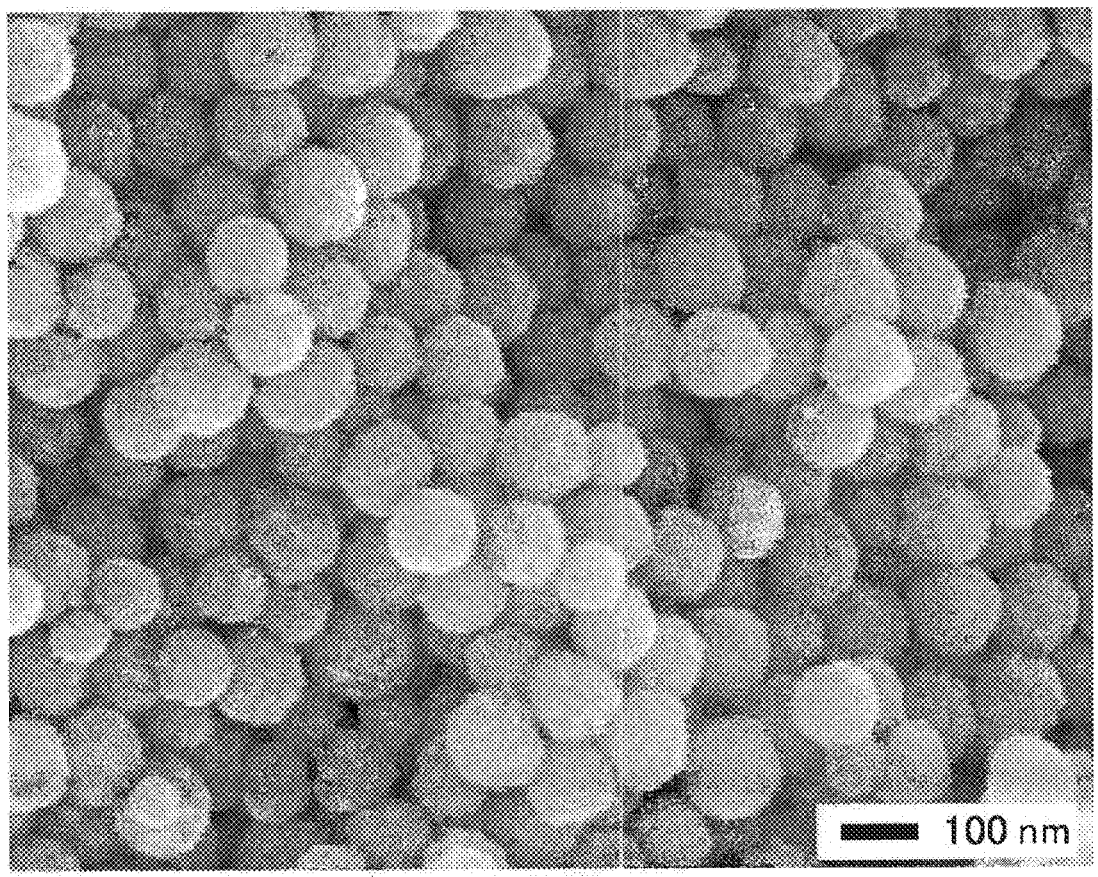
FIG. 3 shows an SEM image of sample 3-2.
Figure 4:
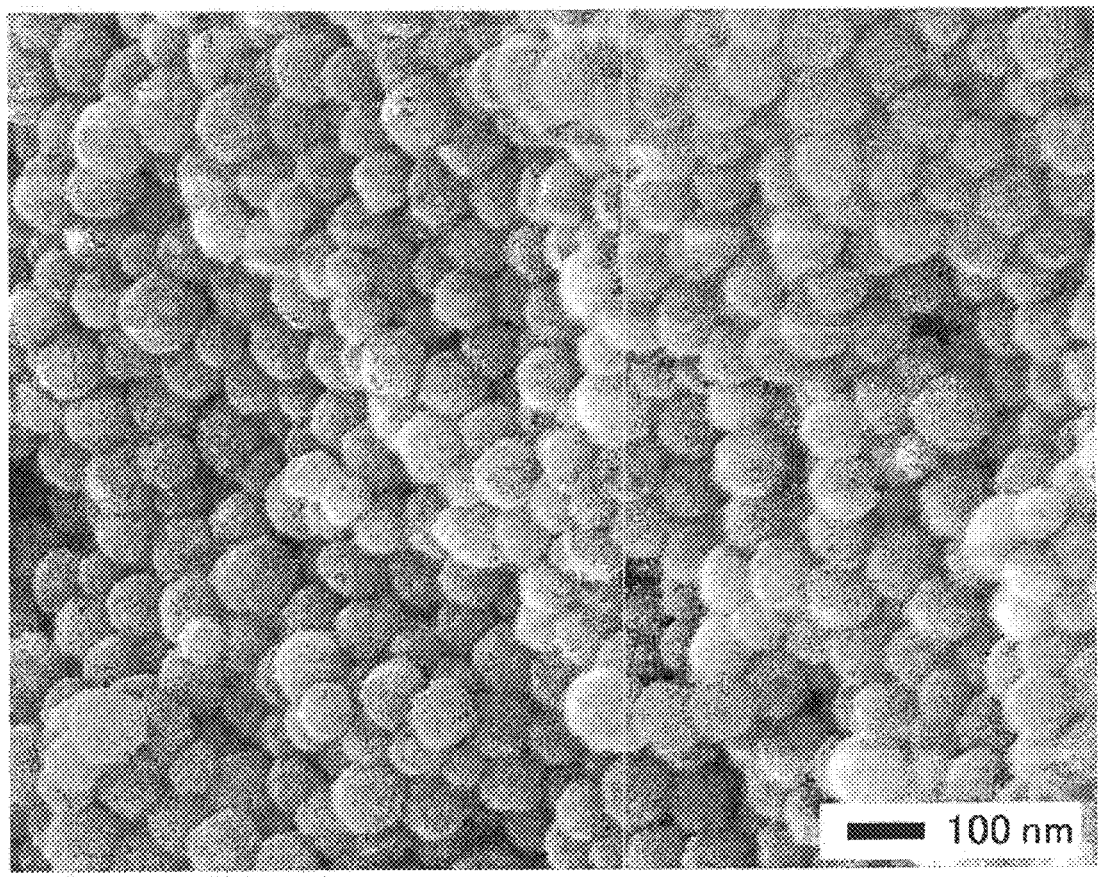
FIG. 4 shows an SEM image of sample 3-3.
Figure 5:
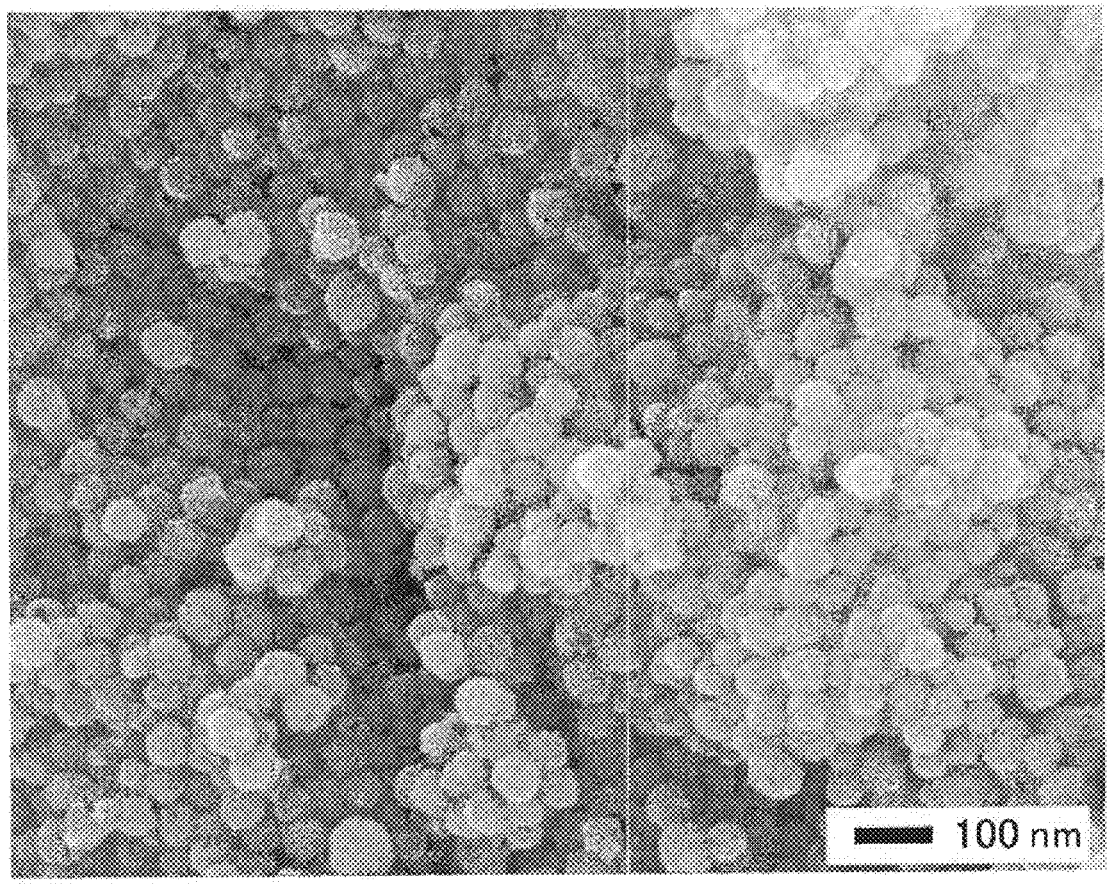
FIG. 5 shows an SEM image of sample 3-4.
Figure 6:
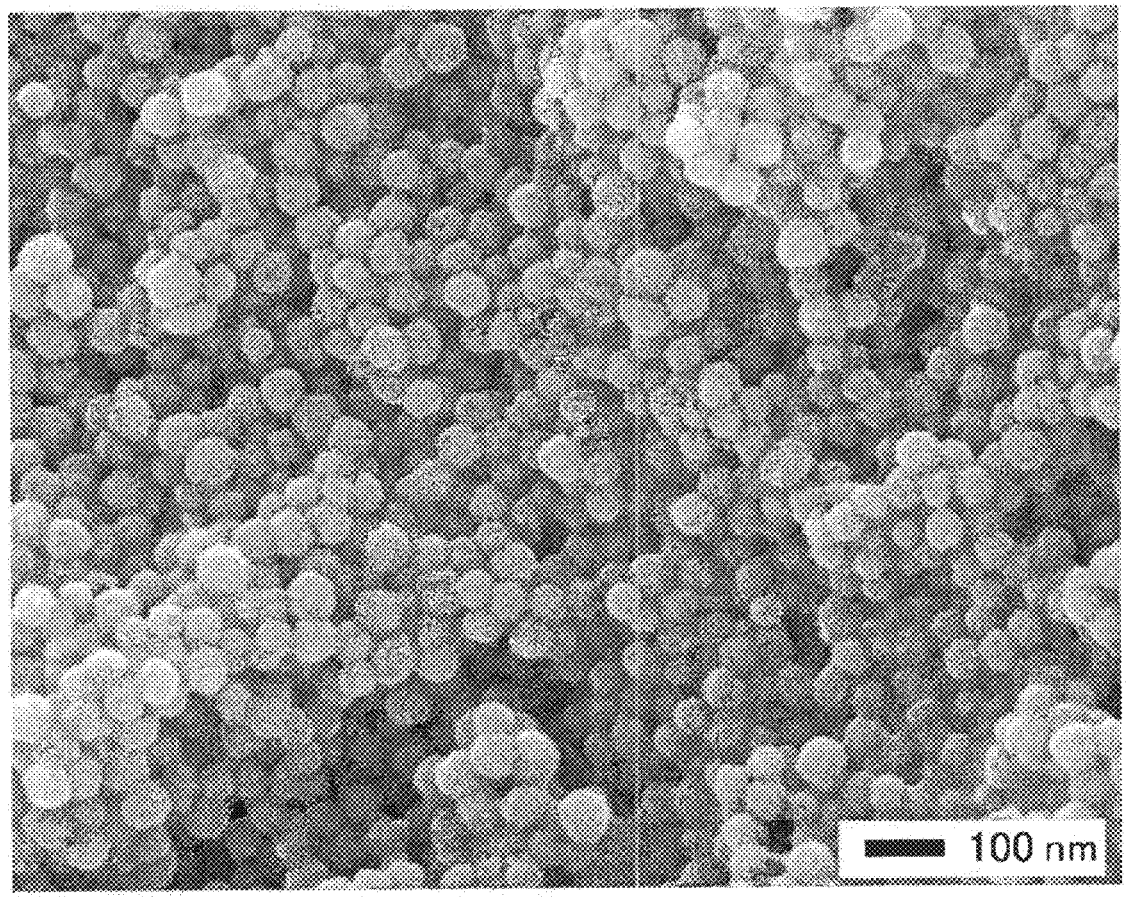
FIG. 6 shows an SEM image of sample 3-5.

As previously noted, in the case of sample 2-4 white turbidity was not produced and a dispersion solution was not obtained. The product was cerium oxide for samples 2-1, 2-2, and 2-3. For sample 2-1, the average particle diameter of the dispersed material was large at 1,330 nm, which was also supported by the SEM results; in addition, sedimentation occurred rapidly with this sample. In contrast, the average particle diameter of the dispersed material was approximately 110 nm for samples 2-2 and 2-3. SEM photographs of samples 2-2 and 2-3 are shown in FIGS. 1 and 2, respectively. Spherical microparticles with a particle diameter of approximately 110 nm were observed, and this average particle diameter agreed with that determined by DLS. These results demonstrated that spherical core-shell-type cerium oxide microparticles with a particle diameter of 110 nm were independently dispersed in the dispersion solution.

It was also shown that a stable dispersion solution was not obtained at a low PVP concentration and that a reaction did not occur at a high PVP concentration, which thus demonstrated that there is an optimal PVP concentration for obtaining a stable core-shell-type cerium oxide microparticle dispersion solution. Based on this example, a PVP concentration from 80 kg/m³ to 105.6 kg/m³ was shown to be satisfactory in this regard. In addition, it was shown in the following example that a PVP concentration of 120 kg/m³ is also sufficient for obtaining a stable cerium oxide microparticle dispersion solution.

TABLE 2

| | | dispersion solution | | powder | |
|---|---|---|---|---|---|
| sample no. | PVP concentration (kg/m³) | average particle diameter by DLS (nm) | stability | product | microparticle shape by SEM observation |
| 2-1 Comp. Ex. | 16 | 1330 | rapid sedimentation | $CeO_2$ | aggregated particles |

TABLE 2-continued

| | | dispersion solution | | powder | |
|---|---|---|---|---|---|
| sample no. | PVP concentration (kg/m³) | average particle diameter by DLS (nm) | stability | product | microparticle shape by SEM observation |
| 2-2 | 80 | 114 | no separation after at least 60 days | $CeO_2$ | spherical |
| 2-3 | 105.6 | 112 | no separation after at least 60 days | $CeO_2$ | spherical |
| 2-4 Comp. Ex. | 160 | | | | |

Example 3

PVP having different average molecular weights was added to 30 cm³ EG (Wako Pure Chemical Industries, Ltd.) with stirring. The catalogue value and the analytical value (by GPC, as polyethylene glycol) for the average molecular weight of the PVP are shown in Table 3. The average molecular weight of the PVP by GPC analysis was increased in the sequence from A to F. The concentration of the added PVP was set at 120 kg/m³. The $Ce(NO_3)_3 \cdot 6H_2O$ concentration was set at 0.600 kmol/m³. The mixture was heated and then heated under reflux for 10 to 30 minutes at 190° C.

For all the samples shown in Table 4, a light brown gas was produced during heating under reflux, after which the solution assumed a white turbidity. A turbid white mixed solution (the dispersion solution) was obtained after heating/refluxing for the prescribed period of time. Dilutions were also prepared by diluting the dispersion solution 10× with ethylene glycol (EG). A portion of the turbid white solution was then subjected to centrifugal separation at from 3,000 rpm to 10,000 rpm in order to remove unreacted materials and the excess PVP and washing with water and ethanol was carried out. Drying the product at 80° C. yielded a powder.

The average particle diameter, viscosity, and long-term stability of the dispersion solution were evaluated by the same methods as described in Example 2. The coefficient of variation c was calculated from c=s/d where d is the average particle diameter and s is the standard deviation determined by DLS with histogram analysis by the Contin method. The particle shape, average particle diameter, and coefficient of variation c were determined for the powder from the results of SEM observation. Product identification was carried out by the same methods as in Examples 1 and 2. The average value of the particle diameters of at least 90 microparticles appearing on the SEM photograph was used as the average particle diameter d. The coefficient of variation c was calculated from c=s/d where the standard deviation s was obtained by determining the particle diameter distribution and determining the standard deviation s thereon. The product was also examined by XRD.

The products for samples 3-1 to 3-6 were all $CeO_2$. According to the SEM observations, the microparticle shape was nonuniform only in the case of sample 3-1, while all of the others were shown to be spherical (FIGS. 3 to 7). A fibrous feature was observed between particles in the SEM photograph of sample 3-6. The average particle diameters determined from the SEM photographs for the spherical samples are shown in Table 4.

The average particle diameter was shown to decline as the molecular weight increased for molecular weights (analytical value by GPC) up to 18,000. In contrast, the particle diameter increased when the molecular weight (analytical value by GPC) exceeded 18,000. The coefficient of variation was 0.15 or less for all of samples 3-2 to 3-6, which demonstrated a narrow particle diameter distribution, i.e., almost a monodisperse condition. It was thus shown that the average particle diameter of an almost monodisperse core-shell-type cerium oxide microparticle could be freely varied by adjusting the molecular weight of the PVP.

Considering now the properties of the dispersion solution, the viscosity of the dispersion solutions for samples 3-1 to 3-6 increased with increasing molecular weight. Excluding samples 3-1 and 3-6, the average particle diameter by DLS was in approximate agreement with the average particle diameter determined from the results of the SEM observations. Thus, it was also shown in Example 3 that spherical core-shell-type cerium oxide microparticles were independently dispersed in the dispersion solution.

Figure 7:
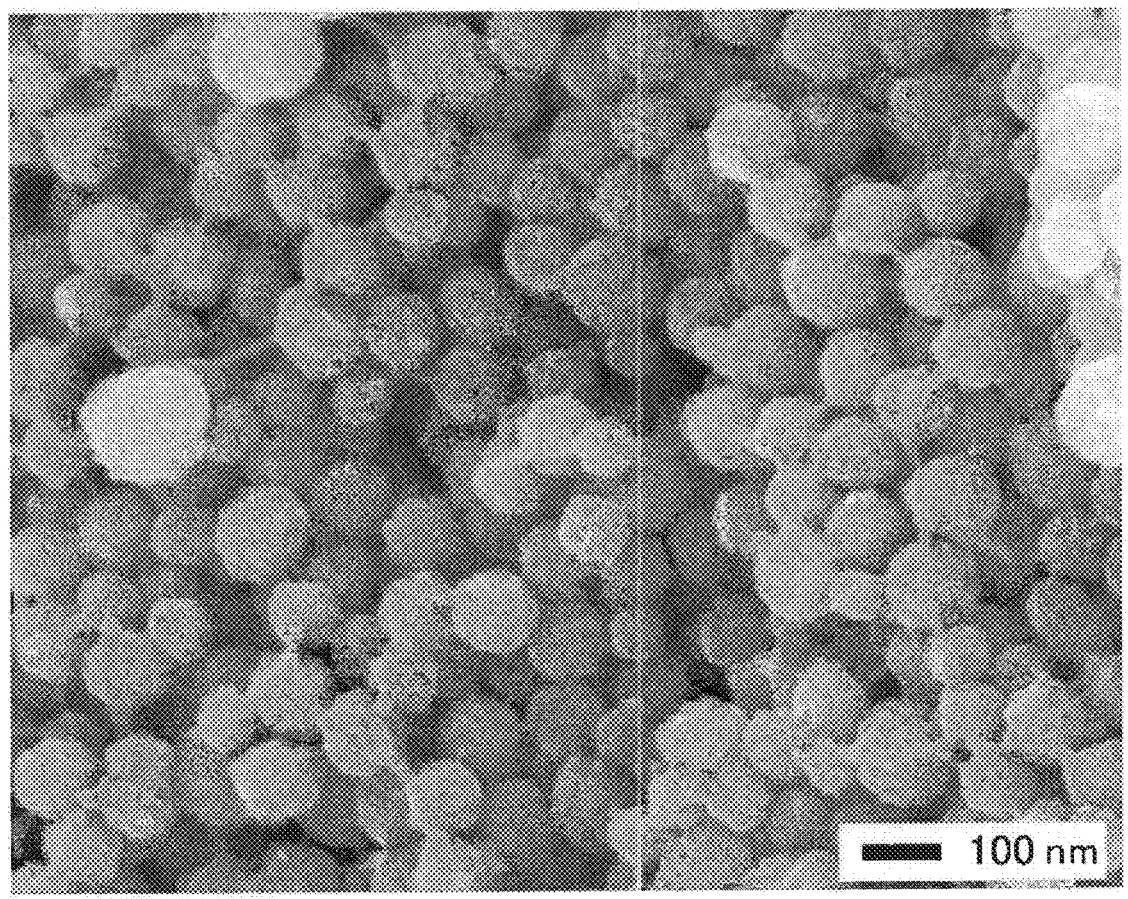
FIG. 7 shows an SEM image of sample 3-6.

Sample 3-1 had a large average particle diameter. This agreed with the microparticle shape being nonuniform and with sample 3-1 being an aggregate. In addition, sample 3-1 underwent rapid sedimentation and was not stable in its dispersion solution form. In the case of sample 3-6, the average particle diameter determined by DLS was larger than the average particle diameter obtained from the results of SEM observation. This is thought to be due to the presence of particle-to-particle bonding by the fibrous feature, as shown in FIG. 7, which led to a large value for the average particle diameter.

TABLE 3

| | molecular weight | | |
|---|---|---|---|
| PVP (polyvinylpyrrolidone) | analytical value by GPC (as polyethylene glycol, weight-average molecular weight) | catalogue value | manufacturer |
| A | 2420 | 3500 | Akros |
| B | 4350 | 10000 | Sigma-Aldrich |
| C | 4790 | 8000 | Akros |
| D | 13900 | 29000 | Sigma-Aldrich |
| E | 18000 | 55000 | Sigma-Aldrich |
| F | 302000 | 360000 | Wako Pure Chemical Industries, Ltd. |

TABLE 4

| | | dispersion solution | | | | | powder | | |
|---|---|---|---|---|---|---|---|---|---|
| | | | DLS method | | | | | | |
| sample no. | PVP (see Table 3) | viscosity (mPa·s) | average particle diameter (nm) | coefficient of variation in particle diameter | stability without dilution | stability diluted 10X with EG | micro-particle shape by SEM observation | average particle diameter (nm) | coefficient of variation in particle diameter | product |
| 3-1 Comp. Ex. | A | 58 | 1220 | 0.187 | X | X | non-uniform shape | | | $CeO_2$ |
| 3-2 | B | 61.1 | 111.2 | 0.065 | ○ | ◉ | spherical | 113.8 | 0.120 | $CeO_2$ |
| 3-3 | C | 61.8 | 85.8 | 0.122 | ○ | ◉ | spherical | 84.3 | 0.146 | $CeO_2$ |
| 3-4 | D | 116.3 | 64.1 | 0.095 | Δ | ◉ | spherical | 57.7 | 0.140 | $CeO_2$ |
| 3-5 | E | 138.3 | 70.3 | 0.199 | Δ | ◉ | spherical | 56.1 | 0.149 | $CeO_2$ |
| 3-6 | F | 3943 | 168.5* | 0.044 | ○ | ◉ | spherical | 100.4 | 0.150 | $CeO_2$ |

◉ no sediment is seen after 1 month
○ small amounts of sediment are seen after 1 month
Δ substantial sediment is seen after 1 month
X sediment is seen in approximately 2 or 3 days
*The measurement result for the undiluted dispersion solution could not be accurately determined due to the high viscosity. The data for the 10X dilution with ethylene glycol (EG) was therefore used.

Example 4

A dispersion solution was prepared using the same method as for sample 3-2 in Example 3 and a dispersion medium replacement test was then run using the following procedure. The dispersion medium and dispersed material were separated by centrifugal separation; terpineol was added to the dispersed material after its separation; and dispersion was carried out using an ultrasound homogenizer. The dispersing time was 4 minutes, and the dispersion process was carried out while cooling.

The average particle diameter was determined by DLS on the dispersion solution after dispersion medium replacement. The result is shown in Table 5. The particle diameter was approximately the same as for sample 3-2. Thus, it was confirmed that the cerium oxide microparticles could also be dispersed in an aggregate-free manner when dispersion medium replacement was carried out. In addition, the stability was extremely good, and separation did not occur even after standing for at least 10 days.

TABLE 5

| | dispersion solution after replacement of the dispersion medium | | | |
|---|---|---|---|---|
| | | DLS method | | |
| sample no. | viscosity (mPa·s) | average particle diameter (nm) | coefficient of variation | stability |
| 4-1 | 45 | 99 | 0.072 | excellent |

Example 5

Characterization by Fourier-transform infrared spectrophotometry (FTIR), thermogravimetry (TG), and transmission electron microscopy (TEM) was carried out on the powder from sample 3-2 of Example 3 (powder provided by separation from the dispersion solution) and on a powder prepared using the same conditions as for sample 3-2 with regard to the cerium nitrate and PVP concentration, but using a different volume of ethylene glycol. According to the TG results, a weight loss of close to 15% was observed around 220° C. Thus, a weight loss was produced at a temperature higher than the boiling point of the dispersion medium (190° C.).

A weight loss of 22 weight % was obtained by heating the dry powder to 900° C. A different sample produced on a different day had a weight loss of 19 weight %, which demonstrated that this weight loss was approximately 19 to 22 weight %. In addition, the FTIR results showed a peak other than the peak assigned to cerium oxide. Excess polymer unassociated with the cerium oxide microparticles had been removed because the dried powder was subjected to centrifugal separation and redispersion in water or ethanol three times. The dispersion medium had also been thoroughly eliminated due to the drying step.

Figure 8:
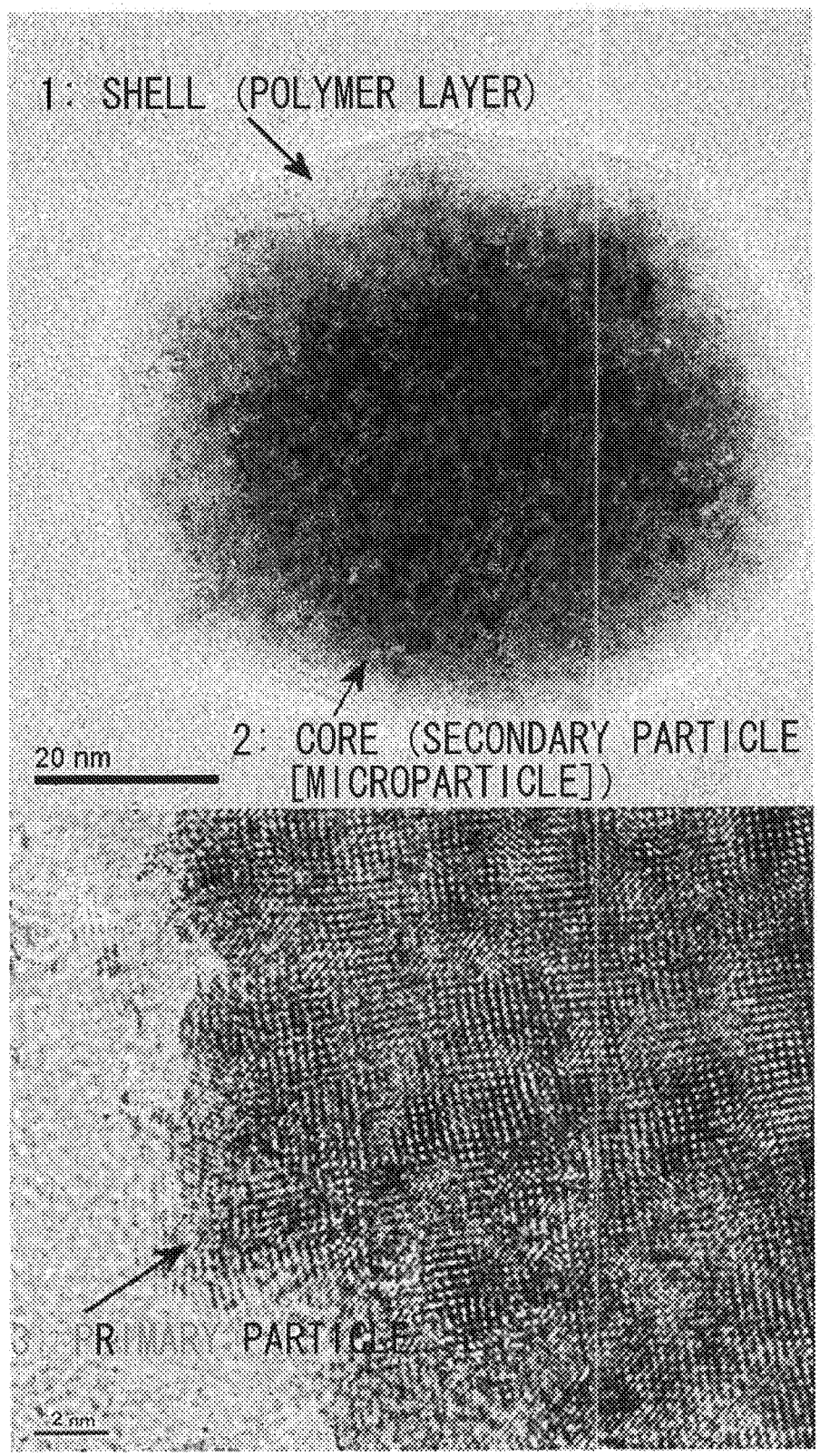
FIG. 8 shows the TEM image for the powder from sample 3-2 and the TEM image for a powder prepared using the same conditions as for sample 3-2 with regard to cerium nitrate and PVP concentration, but using a different volume of ethylene glycol, the image in the lower figure being at higher magnification.

These considerations demonstrated that the non-cerium oxide absorption peak observed by FTIR was caused by a species present on the surface of the core-shell-type cerium oxide microparticle; this was also shown to resemble the absorption of a polymer. The results of the TEM observation are shown in FIG. 8. What appears to be an approximately 5 nm layer of polymer was observed on the particle surface (shell region). The layer was also found to diminish during long-term TEM observation, which suggested degradation by the electron beam. When the preceding observations were considered as a whole, it became clear that polymer was present on the surface of the cerium oxide microparticles, that is, a core-shell-type configuration was present.

Using the Hall method, a value of approximately 3 nm was determined for the crystallite (primary particle) size from the full width at half maximum for the peak in the XRD pattern of the sample 3-2 powder. The results from the TEM observation also gave a primary particle diameter of approximately 1 to 2 nm. The secondary particle was also shown to be a secondary particle yielded by the aggregation of primary particles at high density without gaps among the primary particles. The attachment of PVP on the surface of the cerium oxide microparticles suggests the possibility of a chemically inert ultraviolet blocking agent that does not come into direct contact with the human body.

Example 6

The powder from sample 3-2 of Example 3 (powder provided by separation from the dispersion solution) was redispersed in water, ethanol, terpineol, and ethylene glycol. The powder used for redispersion was the powder after drying. With regard to the proportions of powder and dispersion medium, 5 cm³ dispersion medium was used per 0.1 g powder. The powder was introduced into the dispersion medium and dispersion was carried out using an ultrasound homogenizer. The dispersion time was 3 to 10 minutes and dispersion process was carried out with cooling. A dispersing agent was not used in this process.

After dispersion, the particle diameter of the core-shell-type cerium oxide microparticles in the dispersion solution was examined using DLS. The results are shown in Table 6. Stirring by manually shaking two or three times was performed prior to the measurement. The particle diameter after one day post-dispersion and after eight days post-dispersion was 115 to 135 nm and thus either was the same as the particle diameter of sample 3-2 or was only very slightly larger. Based on these results, it was shown that redispersion could be easily accomplished even with the dried powder and that the average particle diameter of the redispersed cerium oxide microparticles is either the same as or up to 1.3-times the particle diameter determined by SEM observation.

It was thus shown that the spherical cerium oxide microparticles could be redispersed with almost no aggregation. The terpineol-dispersed sample 6-3 presented no separation even after standing for seven days. Even with samples 6-1 and 6-2, in which dispersion was carried out in water and ethanol, respectively, only a slight transparent layer was observed at the top. Uniformity could be rapidly brought about simply by lightly shaking two or three times by hand. These results confirmed that the dispersion solutions provided by redispersion of the dried powder exhibited long-term stability.

TABLE 6

| sample no. | dispersion medium | average particle diameter and coefficient of variation (when stirred immediately prior to measurement) | | | | status of the dispersion solution after standing for 7 days |
|---|---|---|---|---|---|---|
| | | after 1 day post-redispersion | | after 8 days post-redispersion | | |
| | | average particle diameter | coefficient of variation | average particle diameter | coefficient of variation | |
| 6-1 | water | 121.1 | 0.172 | 121.4 | 0.138 | transparent layer for upper 16% |
| 6-2 | ethanol | 115.4 | 0.261 | 116.8 | 0.273 | transparent layer for upper 13% |
| 6-3 | terpineol | 119.5 | 0.131 | 128.6 | 0.133 | no separation |
| 6-4 | ethylene glycol | 100.8 | 0.221 | 104.4 | 0.135 | no separation |

Example 7

PVP (PVP B in Table 3) and Ce(NO$_3$)$_3$·6H$_2$O (Kojundo Chemical Laboratory Co., Ltd.) were added to 30 cm³ EG (Wako Pure Chemical Industries, Ltd.) with stirring. The concentration of the added PVP was set at 120 kg/m³. The concentration of the Ce(NO$_3$)$_3$·6H$_2$O was set at 0.600 kmol/m³. The mixture was heated and then heated under reflux for 120 minutes at 190° C. These production conditions are the same as for sample 1-5 in Example 1. A light brown gas was produced during heating under reflux, after which the solution assumed a white turbidity. A turbid white mixed solution (the dispersion solution) was obtained after heating/refluxing for the prescribed period of time. A portion of the turbid white solution was then subjected to centrifugal separation at 18,000 rpm in order to remove unreacted materials and the excess PVP and washing with water and ethanol was carried out. Drying the product at 80° C. yielded a powder.

The results in Table 7 were determined using the same methods as described in Examples 2 and 3. As also indicated in Example 1, the product was cerium oxide. The average particle diameter determined by DLS was 110 nm. The average particle diameter determined by SEM observation was approximately 130 nm, which was approximately the same as the particle diameter determined by DLS. These results demonstrated that spherical core-shell-type cerium oxide microparticles were present without aggregation.

Whether the heating/refluxing time was 30 minutes or less or was 120 minutes, there was almost no difference—to such a degree that the particle diameter was only slightly increased—in the properties of the obtained microparticles. However, the former provided a low weight for the obtained microparticles. That is, the yield was poor. Extending the heating/refluxing time resulted in little unreacted cerium ion and increased the resulting microparticle weight.

Figure 9:
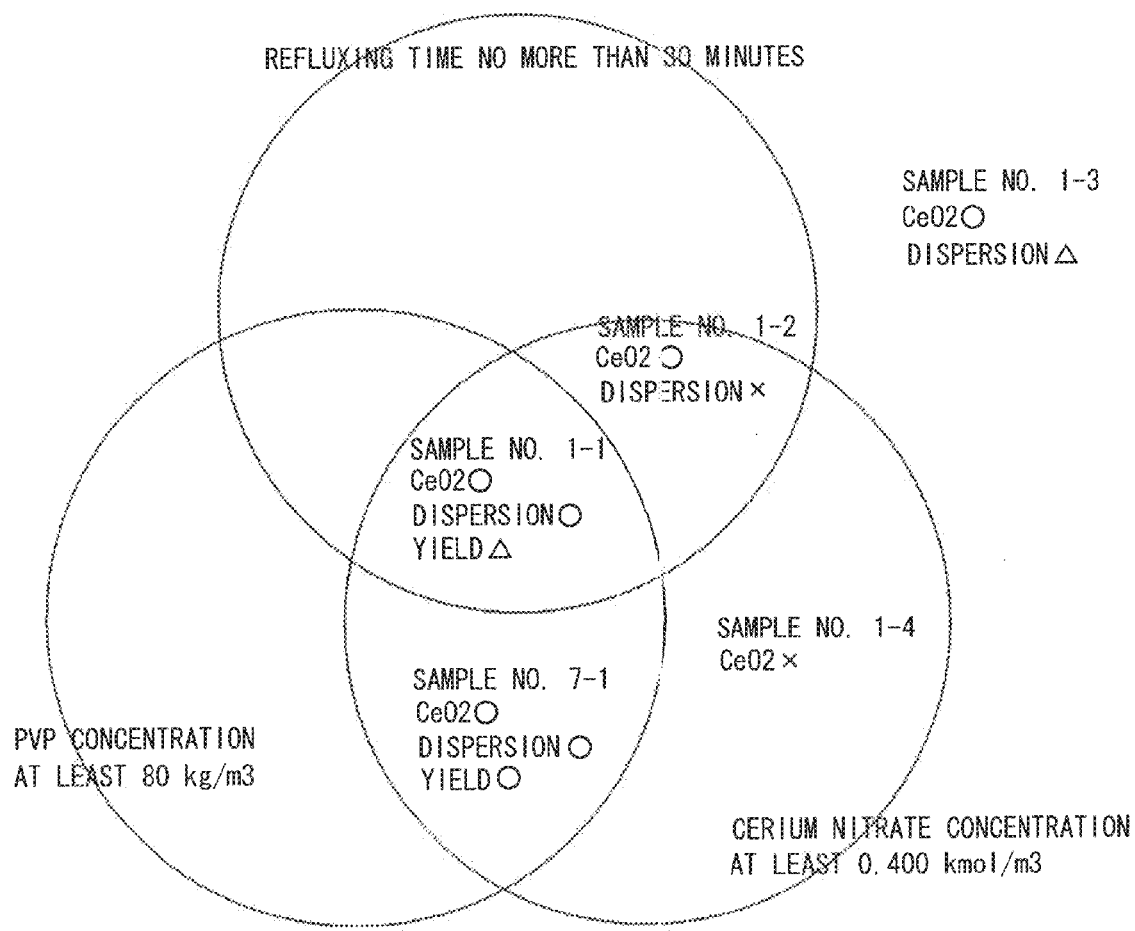
FIG. 9 shows the relationships between the experimental conditions and the microparticles and dispersion solutions obtained as a result.

The relationships between the experimental conditions and the microparticles and dispersion solutions obtained as a result are shown in FIG. 9. For a cerium nitrate concentration of at least 0.400 kmol/m³, a PVP concentration of at least 80 kg/m³ is the essential condition for obtaining microparticles of cerium oxide and obtaining an excellent dispersibility. A PVP concentration of at least 80 kg/m³ and a heating/refluxing time of more than 30 minutes are the essential conditions for obtaining microparticles of cerium oxide in a good yield and obtaining an excellent dispersibility.

TABLE 7

| sample no. | dispersion solution | | | | | powder | | |
|---|---|---|---|---|---|---|---|---|
| | | DLS method | | | | | coefficient | |
| | viscosity (mPa·s) | average particle diameter (nm) | coefficient of variation in particle diameter | stability | microparticle shape by SEM observation | average particle diameter (nm) | of variation in particle diameter | product |
| 7-1 | 32.9 | 110.1 | 0.286 | excellent | spherical | 131.9 | 0.160 | $CeO_2$ |

Example 8

The average particle diameter in the following dispersion solutions was determined by DLS: the redispersion solution (sample 8-1) provided by the redispersion in water of the powder obtained in Example 7, and the redispersion solution (sample 8-2) provided by the redispersion in water of a powder itself provided by subjecting the powder obtained in Example 7 to a heat treatment once in air at 300° C. for 4 hours. The results are shown in Table 8. The dispersion solution was obtained by adding 0.1 g of the powder to 5 cm$^3$ water and dispersing for 10 minutes using an ultrasound homogenizer.

For both sample 8-1 and sample 8-2, the average particle diameter in the dispersion solution was no more than 1.2-times the particle diameter determined by SEM observation, which demonstrated that there was almost no aggregation of the core-shell-type cerium oxide microparticles in the dispersion solution. This showed that the excellent dispersibility of the powder was maintained even after being subjected to a heat treatment. The FTIR results for the powder subjected to a heat treatment in air for 4 hours at 300° C. or 500° C. suggested that a very thin layer of an organic compound or polymer having a structure about the same as that on the non-heat-treated powder was also attached to the surface of the powder that had been heat treated in air for 4 hours at 300° C. or 500° C. The maintenance of the dispersibility is thought to be due to the presence of this attached polymer or organic compound.

TABLE 8

| sample no. | average particle diameter (nm) | coefficient of variation in particle diameter |
|---|---|---|
| 8-1 | 152.2 | 0.262 |
| 8-2 | 139.3 | 0.226 |

Example 9

Hydroxypropyl cellulose (HPC) (from Wako Pure Chemical Industries, Ltd., molecular weight: 15,000 to 30,000) and $Ce(NO_3)_3 \cdot 6H_2O$ (Kojundo Chemical Laboratory Co., Ltd.) were added to 30 cm$^3$ EG (Wako Pure Chemical Industries, Ltd.) with stirring. The concentration of the added HPC was set at 120 kg/m$^3$. The concentration of the $Ce(NO_3)_3 \cdot 6H_2O$ was set at 0.600 kmol/m$^3$. The mixture was heated and then heated under reflux for 10 minutes at 190° C. A light brown gas was produced during heating under reflux, after which the solution assumed a white turbidity. A turbid white mixed solution (the dispersion solution) was obtained after heating/refluxing for the prescribed period of time. A portion of the turbid white solution was then subjected to centrifugal separation at 18,000 rpm in order to remove unreacted materials and the excess HPC and washing with water and ethanol was carried out. Drying the product at 80° C. yielded a powder.

Figure 10:
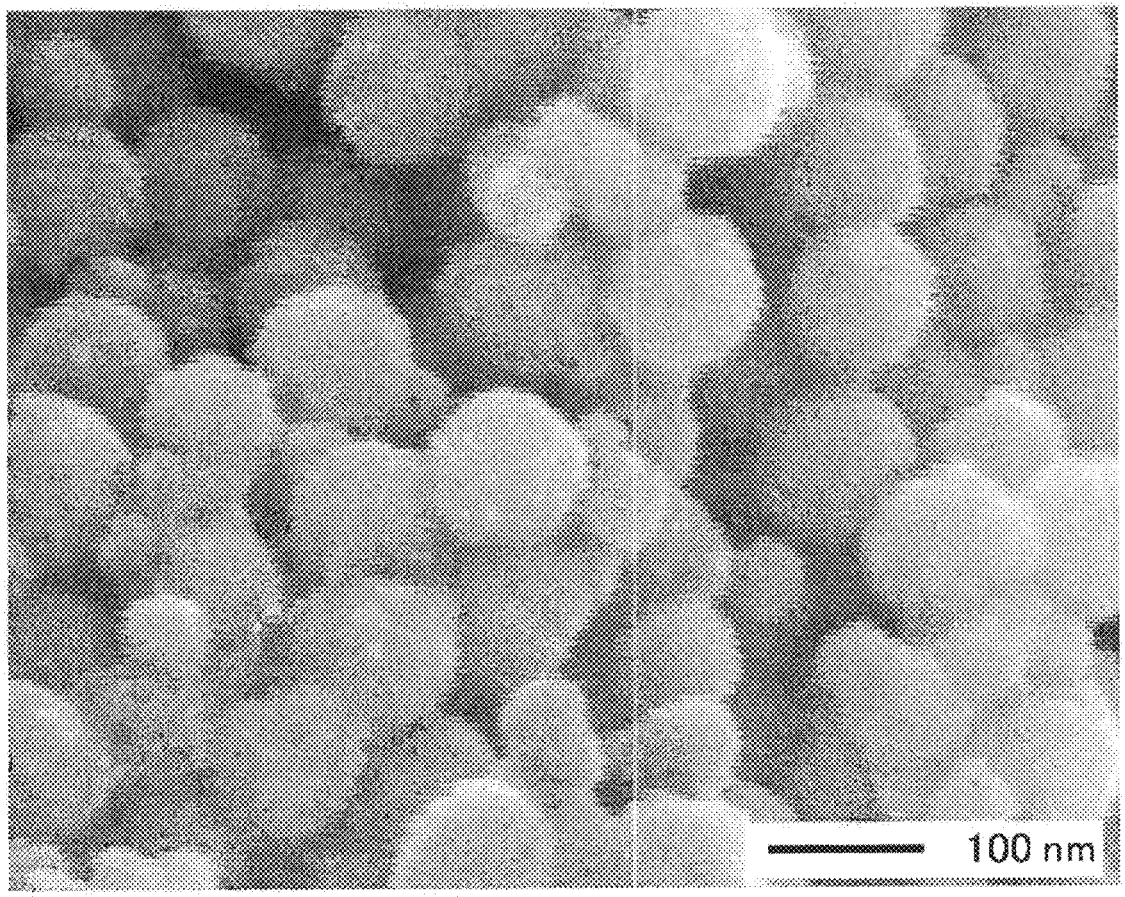
FIG. 10 shows an SEM image of sample 9-1.

The results shown in Table 9 were determined by the same methods as described in Examples 2 and 3. The product was confirmed to be cerium oxide by XRD. The microparticle shape was confirmed to be spherical by SEM observation of the powder (FIG. 10). The average particle diameter was 90.1 nm, and the coefficient of variation in average particle diameter was 0.223. The average particle diameter in the dispersion solution was 170.6 nm, which was approximately 1.89 times the average particle diameter determined by SEM observation. This demonstrated that a stable dispersion solution is also obtained when synthesis is carried out using HPC in place of PVP, although the particle diameter in the dispersion solution is larger than for the use of PVP.

TABLE 9

| sample no. | dispersion solution | | | | | powder | | |
|---|---|---|---|---|---|---|---|---|
| | | DLS method | | | | | coefficient | |
| | viscosity (mPa·s) | average particle diameter (nm) | coefficient of variation in particle diameter | stability (2 weeks) | microparticle shape by SEM observation | average particle diameter (nm) | of variation in particle diameter | product |
| 9-1 | 235.4 | 170.6 | 0.182 | excellent | spherical | 90.1 | 0.223 | $CeO_2$ |

Example 10

Figure 11:
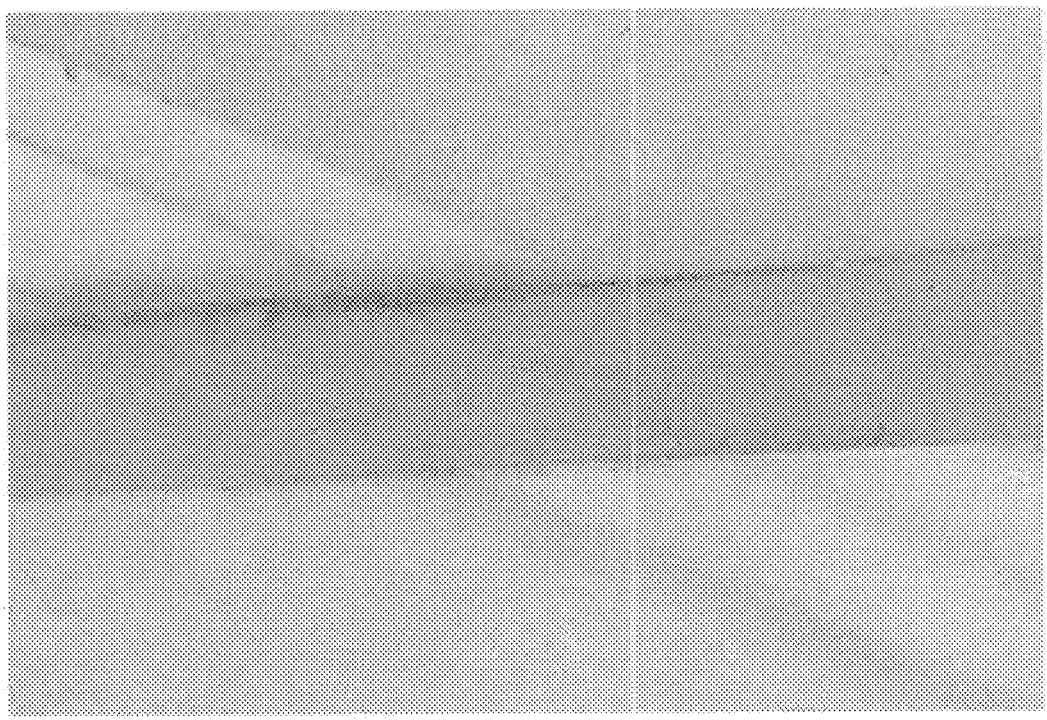
FIG. 11 shows an optical microscope image of sample 10-1.
Figure 12:
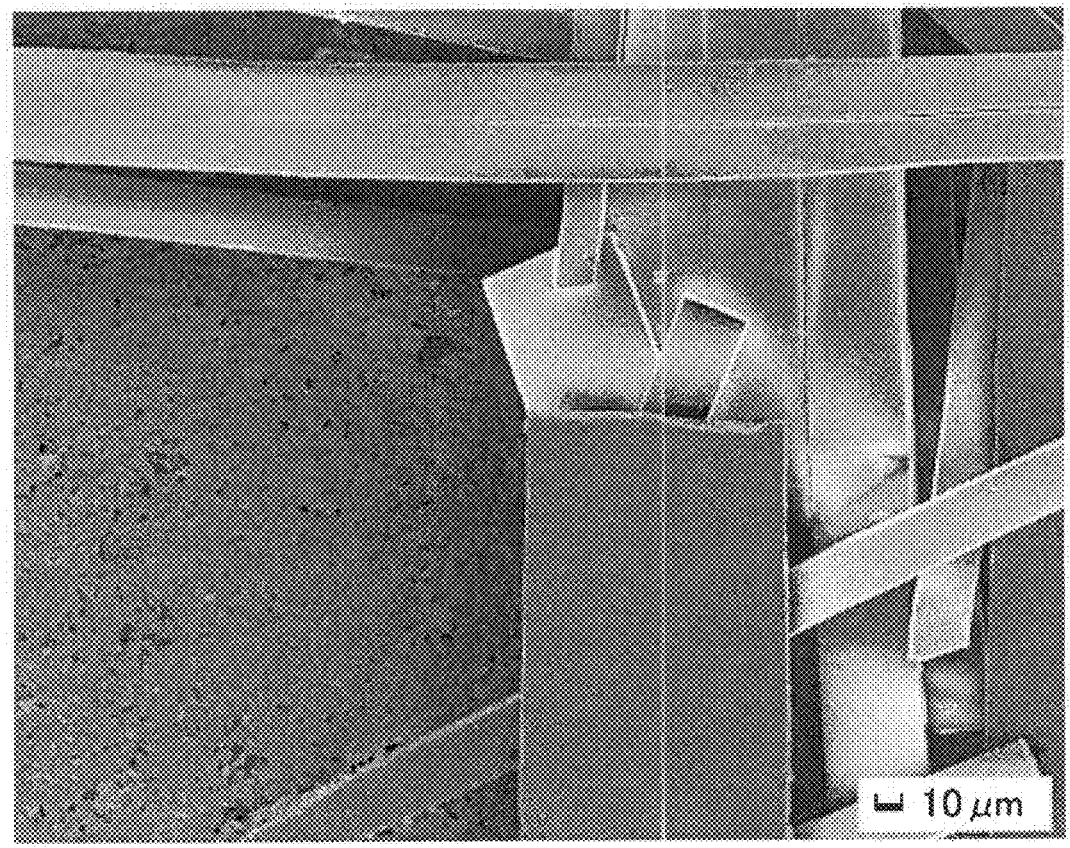
FIG. 12 shows an SEM image of sample 10-1.

An acicular crystalline sample (sample 10-1) was obtained by heating 6-2 from Example 6 at 50° C. to evaporate the ethanol. The results of observation with an optical microscope are shown in FIG. 11 and the results of SEM observation are shown in FIG. 12. The cerium oxide microparticles are shown by FIGS. 11 and 12 to be three dimensionally aggregated. In addition, a crack in the underlying aggregate can be seen through the upper aggregate in FIG. 11. The conclusion can therefore be drawn that this aggregate is transparent to visible light.

Figure 13:
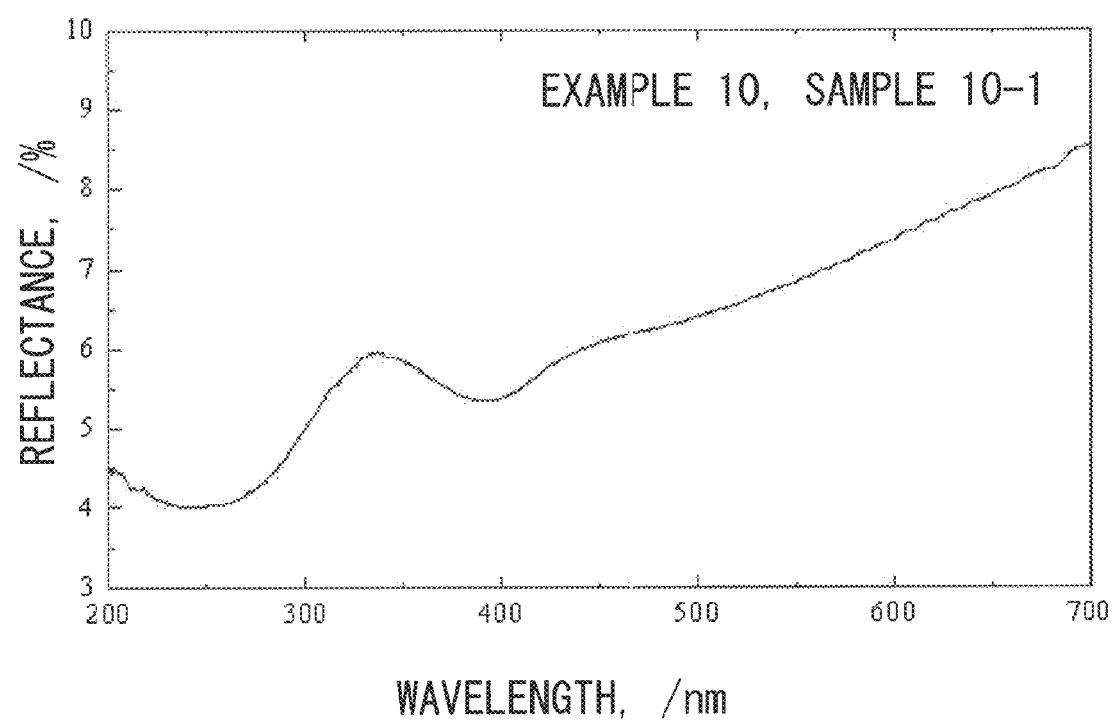
FIG. 13 shows the results of measurement on sample 10-1 using an ultraviolet-visible-near infrared microspectrophotometer.

The results of measurement of the reflectance by sample 10-1 in the ultraviolet-visible region are shown in FIG. 13; this measurement was performed with an ultraviolet-visible-near infrared microspectrophotometer. A peak occurs in the vicinity of 333 nm. This is thought to be a peak due to the periodic arrangement of the cerium oxide microparticles. This indicated a high likelihood that sample 10-1 was a photonic crystal.

Example 11

Figure 14:
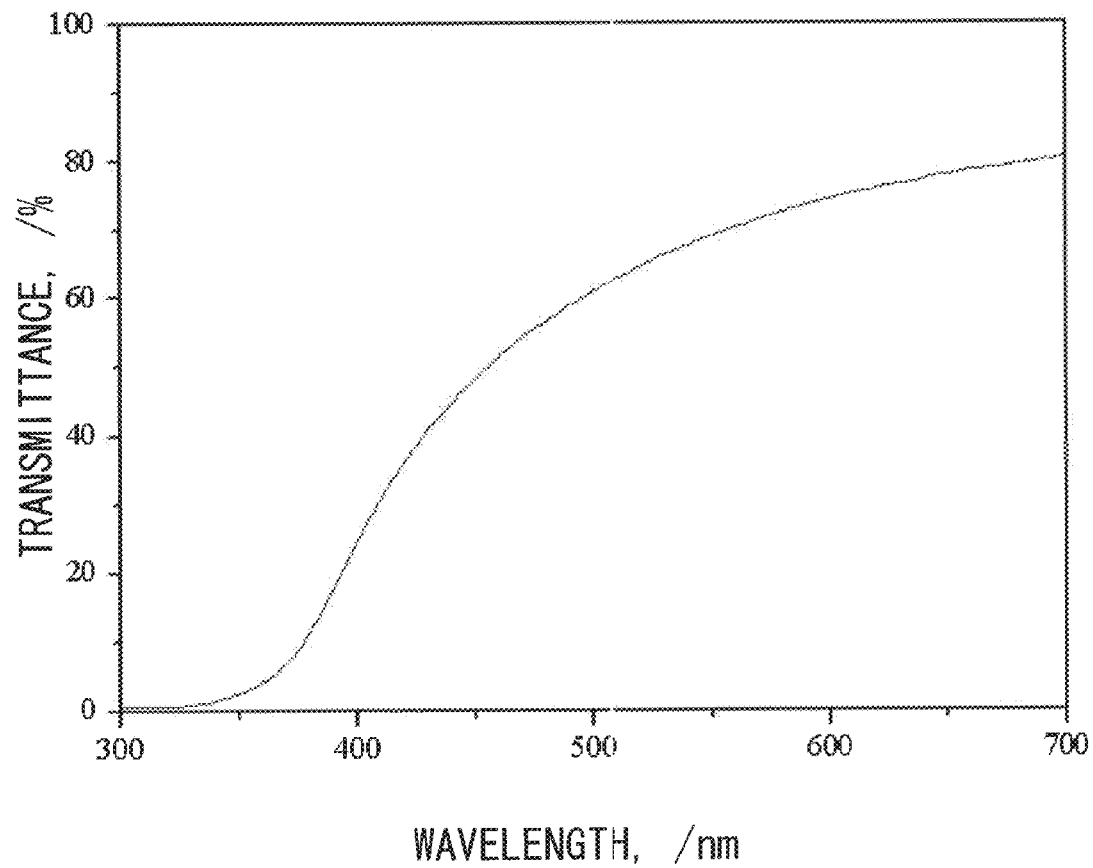
FIG. 14 shows the results of measurement, using an ultraviolet-visible-near infrared spectrophotometer, on a thin film on quartz glass, prepared from the dispersion solution of sample 8-1.

A thin film was produced on quartz glass using a dispersion solution prepared by the same method as for the sample 8-1 that was used in Example 8. The result of measurement of the ultraviolet-visible light absorption spectrum on this thin film is shown in FIG. 14. There was almost no transmission of light in the ultraviolet region at 400 nm and below, that is, this light was absorbed. This confirmed that the cerium oxide microparticles had an ultraviolet blocking activity.

Example 12

Figure 15:
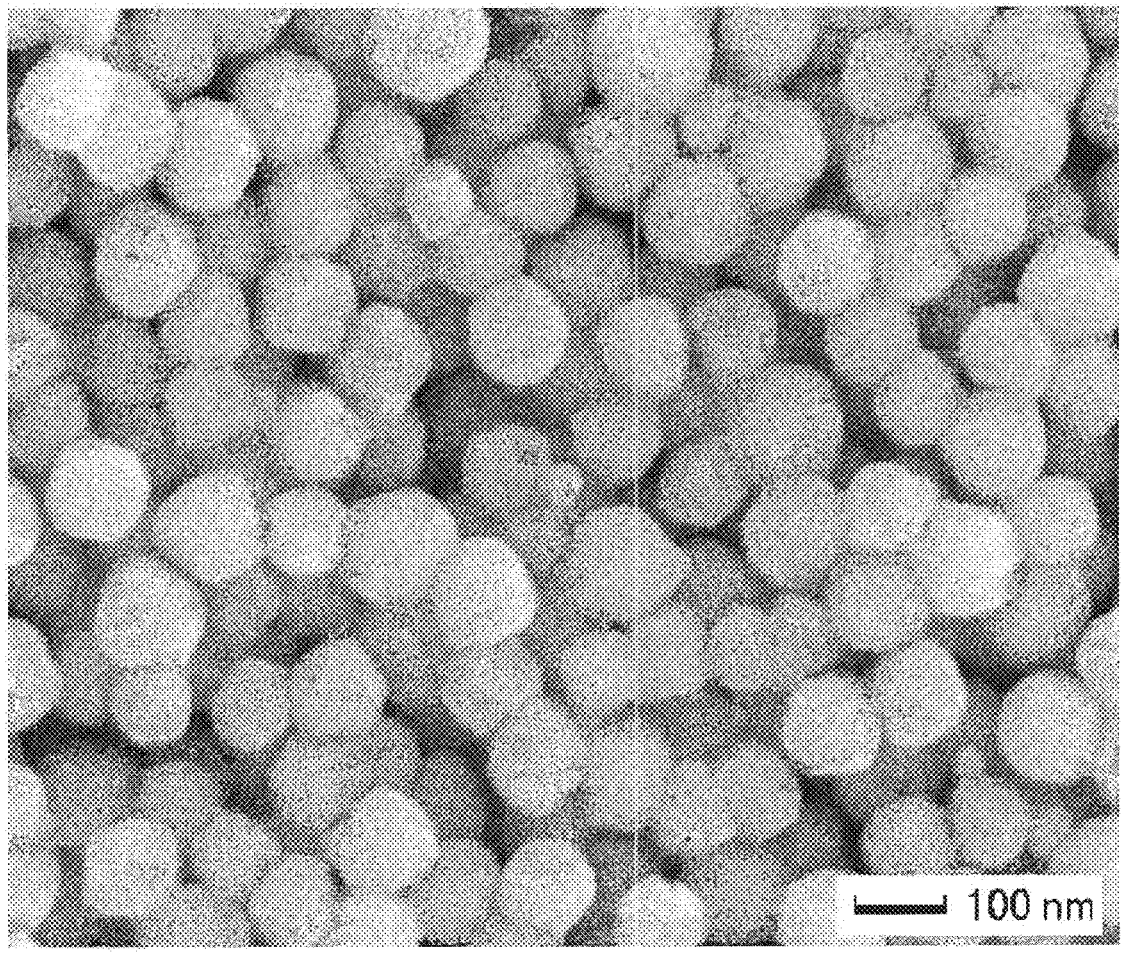
FIG. 15 shows the microstructure of a baked thick film.

A screen printing paste was prepared from a cerium oxide microparticle dispersion solution, and this screen printing paste was used to form a thick film on a substrate by screen printing. The resulting thick film was baked at 1000° C. to obtain a baked thick film formed on the substrate. The microstructure of the baked thick film is shown in FIG. 15. This baked thick film is shown to be a porous thick film of particles that have uniform particle diameters.

Figure 16:
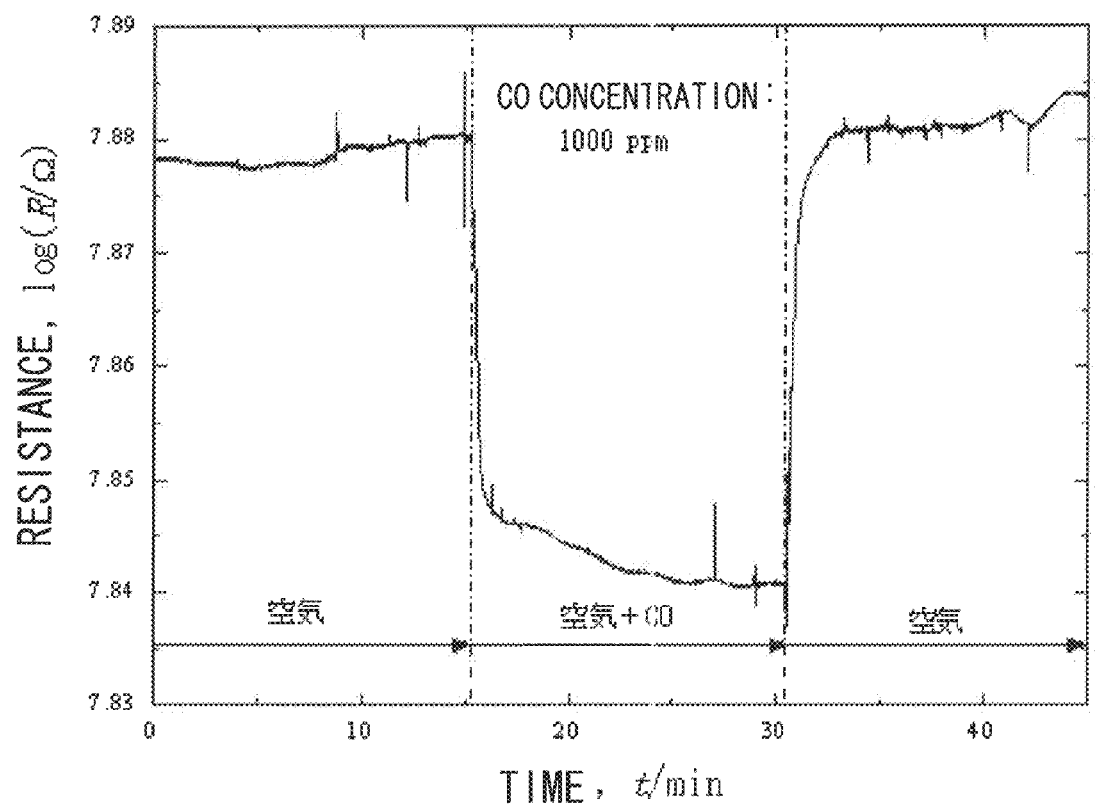
FIG. 16 shows the change in the resistance of a baked thick film, when the atmosphere was switched from air to carbon monoxide-containing air.

An electrode was disposed in advance on the substrate. The baked thick film was heated to a prescribed temperature and its resistance was then measured in the air. Air containing carbon monoxide gas was subsequently introduced and the change in the resistance was monitored. The results are reported in FIG. 16. The resistance rapidly declined when the carbon monoxide-containing air was introduced. The original resistance was quickly restored when a switch was made to air that did not contain carbon monoxide. These observations confirmed that a porous thick film prepared from core-shell-type cerium oxide microparticles according to the present invention could function as a gas sensor.

Example 13

Figure 17:
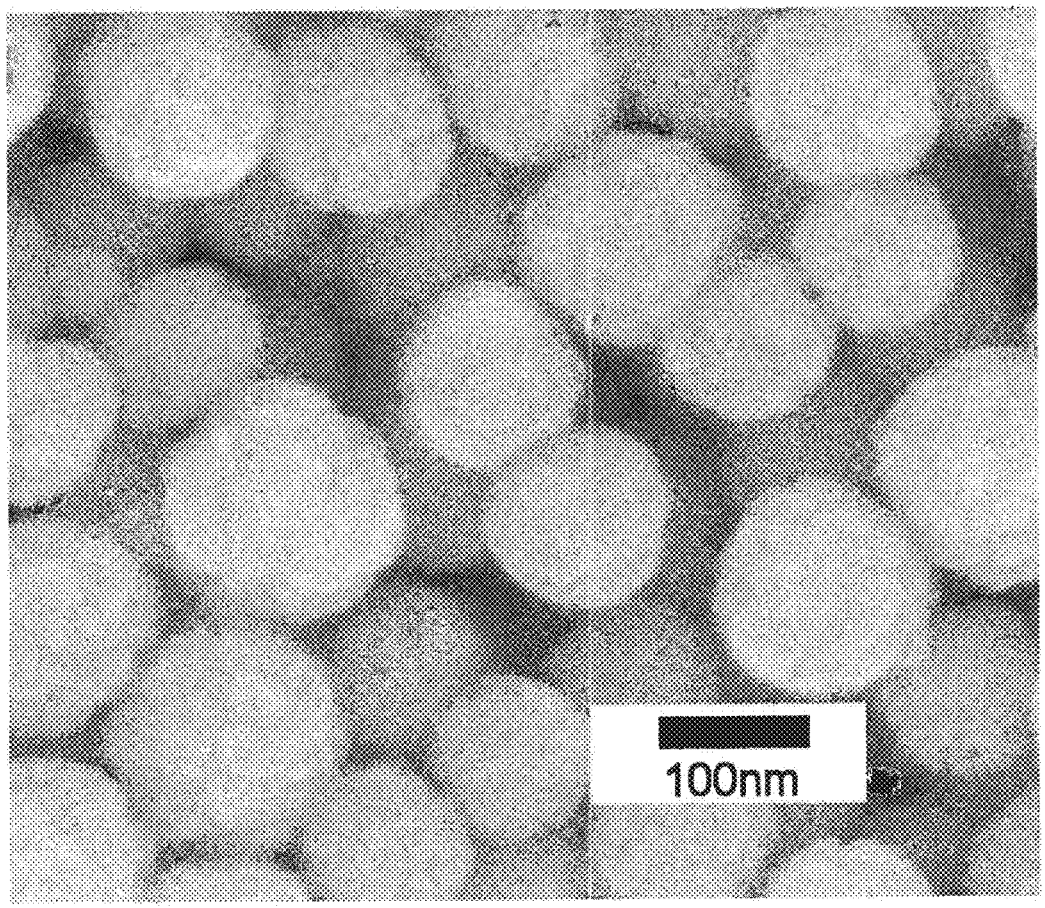
FIG. 17 shows the SEM image of sample 13-1, which comprised the cerium oxide microparticles (only the secondary particles) of just the core portion.

Sample 13-1 was prepared as follows: a powder was prepared by the same method as used to prepare sample 3-2 in Example 3, but in this instance using a heating/refluxing time of 120 minutes; this powder was additionally subjected to a heat treatment in air for 2 hours at 800° C. to give sample 13-1. The results of SEM observation of sample 13-1 are shown in FIG. 17. At this temperature the polymer layer undergoes an almost complete combustion and almost no polymer layer remains on the powder. As a consequence, the SEM image is an SEM image of cerium oxide microparticles that no longer have a core-shell configuration, but rather are almost the core by itself. The cerium oxide microparticles in this case were shown to be spherical and to be of almost uniform size.

Example 14

PVP (catalogue value for the average molecular weight is 10,000, from Sigma-Aldrich) and $Ce(NO_3)_3 \cdot 6H_2O$ (Kojundo Chemical Laboratory Co., Ltd.) were added to 30 $cm^3$ EG (Wako Pure Chemical Industries, Ltd.) with stirring. The concentration of the added PVP was set at 120 $kg/m^3$. The concentration of the $Ce(NO_3)_3 \cdot 6H_2O$ was set at 0.600 $kmol/m^3$.

The mixture was heated and then heated under reflux; the heating/reflux temperature was varied from sample to sample. The experimental conditions are shown in Table 10. In the case of samples 14-1 to 14-5, the liquid was a turbid white liquid after heating under reflux, and for this reason the microparticles were separated from the dispersion solution by more or less the same method as in Example 2 and were characterized by SEM and XRD. In the case of samples 14-6 and 14-7, white turbidity was not present even after the heating under reflux. Sample 14-6 was subjected to drying at 150° C. using a dryer or drying at 80° C. using an evaporator; this was followed by characterization by SEM and XRD. The solvent was rapidly evaporated at 150° C. and a dry material was obtained.

TABLE 10

| sample no. | heating · refluxing temperature (° C.) | heating · refluxing time (min) | time for initial appearance of white turbidity (min) | status of liquid after heating · refluxing | particle shape by SEM observation | average particle diameter as determined by SEM (nm) | results of XRD analysis |
|---|---|---|---|---|---|---|---|
| 14-1 | 190 | 15 | 5 | white turbidity | spherical | 76 | $CeO_2$ |
| 14-2 | 160 | 45 | 14 | white turbidity | spherical | 82 | $CeO_2$ |
| 14-3 | 140 | 120 | 40 | white turbidity | spherical | 149 | $CeO_2$ |
| 14-4 | 120 | 1320 | 180 | white turbidity | spherical | 85 | $CeO_2$ |
| 14-5 | 110 | 1320 | at least 300 minutes | white turbidity | spherical | 73 | $CeO_2$ |

TABLE 10-continued

| sample no. | heating · refluxing temperature (° C.) | heating · refluxing time (min) | time for initial appearance of white turbidity (min) | status of liquid after heating · refluxing | particle shape by SEM observation | average particle diameter as determined by SEM (nm) | results of XRD analysis |
|---|---|---|---|---|---|---|---|
| 14-6 Comp. Ex. | 100 | 1320 | white turbidity not present | transparent | spherical particles are not seen | spherical particles are absent | $CeO_2$ |
| 14-7 Comp. Ex. | 90 | 1320 | white turbidity not present | transparent | | | |

As may be understood from Table 10, the results for a heating/refluxing temperature of at least 110° C. were clearly different from the results for a heating/refluxing temperature of 100 and below. According to Table 10, more time was required for the initial appearance of white turbidity as the heating/refluxing temperature declined from 190° C. In addition, more time was required at lower temperatures to produce strong turbidity. Spherical particles were observed at all heating/refluxing temperatures greater than or equal to 110° C., and it was shown that core-shell-type microparticles were obtained.

In contrast, white turbidity did not appear at temperatures of 100 or less even when heating/refluxing was carried out for 22 hours. After heating under reflux, the solution (dispersion solution) had a transparent appearance and could not be said to exhibit white turbidity. The diffraction peaks for cerium oxide ($CeO_2$) were seen in the XRD pattern of the powder obtained by drying sample 14-6 at 150° C., and the diffraction peaks for cerium oxide ($CeO_2$) were also seen, although very weakly, in the XRD pattern of the powder obtained by drying at 80° C. using an evaporator.

These results confirmed the presence of cerium oxide in the powders. Core-shell-type particles were not seen in the SEM observation of the powder obtained by drying sample 14-6 at 150° C. Based on these results, the obtained powder is considered to be a composite composition of the oxide and polymer. The preceding demonstrated that core-shell-type microparticles were not obtained when the heating/refluxing temperature was below 110° C. Or, when stated in the reverse manner, a temperature of at least 110° C. was shown to be required in order to obtain core-shell-type cerium oxide microparticles.

INDUSTRIAL APPLICABILITY

As has been described above, the present invention relates to a core-shell-type cerium oxide microparticle, a dispersion solution containing this core-shell-type cerium oxide microparticle, and a process of producing this core-shell-type cerium oxide microparticle and its dispersion solution. The present invention can provide spherical core-shell-type cerium oxide microparticles that have a particle diameter from about 50 nm to 200 nm, that exhibit a small particle diameter distribution (standard deviation on the particle diameter), and that exhibit an excellent dispersibility in liquids; the present invention can also provide a dispersion solution of these core-shell-type cerium oxide microparticles. The present invention can additionally provide a convenient process of producing the aforementioned core-shell-type cerium oxide microparticles and a convenient process of producing dispersion solutions of these core-shell-type cerium oxide microparticles. The present invention is useful for providing cerium oxide microparticles, a dispersion solution containing cerium oxide microparticles, and a process of producing the preceding, that can be used for applications such as, for example, catalysts, photonic crystals, gas sensors, chemical-mechanical polishes, ultraviolet blocking agents, and so forth.

The invention claimed is:

1. A process of producing core-shell cerium oxide microparticles having a cross-linked polymer layer on a spherical aggregation of primary nanosize particles, comprising:
    mixing a cerium (III) nitrate hydrate and a polymer of polyvinylpyrrolidone (PVP), which has an average molecular weight of 4,000 to 20,000 in terms of polyethylene glycol, in a high-boiling organic solvent to obtain a mixture having a concentration of the polymer of 80 kg/m3 to 120 kg/m3; and
    heating the mixture under reflux at a temperature ranging from 110° C. to 190° C. to give the core-shell cerium oxide microparticles.

2. The process according to claim 1, wherein the concentration of the polymer is 80 kg/$m^3$ to 105.6 kg/$m^3$.

3. The process according to claim 1, wherein the concentration of the polymer is 80 kg/$m^3$.

4. The process according to claim 1, wherein the concentration of the polymer is 120 kg/$m^3$.

5. The process according to claim 1, wherein the heating under refluxing is performed for about 10 to 120 minutes.

6. The process according to claim 1, wherein the heating under reflux is performed for more than 30 minutes.

7. The process according to claim 1, wherein the concentration of the cerium (III) nitrate hydrate in the mixture is at least 0.400 kmol/$m^3$.

8. The process according to claim 1, wherein the concentration of the cerium (III) nitrate hydrate in the mixture is 0.400 kmol/$m^3$.

9. The process according to claim 1, wherein the concentration of the cerium (III) nitrate hydrate in the mixture is 0.600 kmol/$m^3$.

10. The process according to claim 1, wherein the concentration of the cerium (III) nitrate hydrate in the mixture is 0.400-0.600 kmol/$m^3$.

11. The process according to claim 1, wherein the high-boiling organic solvent is ethylene glycol.

12. A process of producing core-shell cerium oxide microparticles having a cross-linked polymer layer on a spherical aggregation of primary nanosize particles, comprising:
    mixing a cerium (III) nitrate hydrate and a polymer of polyvinylpyrrolidone (PVP), which has an average molecular weight of 4,000 to 20,000 in terms of polyethylene glycol, in a high-boiling organic solvent to obtain a mixture having a concentration of the polymer of 80 kg/m3 to 120 kg/m3 and a concentration of the cerium (Ill) nitrate hydrate of at least 0.400 kmol/m3; and heating the mixture under reflux at a temperature ranging from 110° C. to 190° C. to give the core-shell cerium oxide microparticles.

13. A process of producing core-shell cerium oxide microparticles having a cross-linked polymer layer on a spherical aggregation of primary nanosize particles comprising:

mixing a cerium (III) nitrate hydrate and a polymer of polyvinylpyrrolidone (PVP), which has an average molecular weight of 4,000 to 20,000 in terms of polyethylene glycol, in a high-boiling organic solvent to obtain a mixture having a concentration of the polymer 80 kg/m3 to 120 kg/m3; and heating the mixture under reflux at a temperature ranging from 110° C. to 190° C. for more than 30 minutes to give the core-shell cerium oxide microparticles.

14. A process of producing core-shell cerium oxide microparticles having a cross-linked polymer layer on a spherical aggregation of primary nanosize particles comprising:

mixing a cerium (III) nitrate hydrate and a polymer of polyvinylpyrrolidone (PVP), which has an average molecular weight of 4,000 to 20,000 in terms of polyethylene glycol, in a high-boiling organic solvent to obtain a mixture having a concentration of the polymer of 80 kg/m3 to 120 kg/m3 and a concentration of the cerium 0ID nitrate hydrate of 0.400 kmol/m3 to 0.600 kmol/m3; and heating the mixture under reflux at a temperature ranging from 110° C. to 190° C. for 10 to 120 minutes to give the core-shell cerium oxide microparticles.

* * * * *